(12) United States Patent
Sarrafzadeh et al.

(10) Patent No.: US 9,398,879 B2
(45) Date of Patent: Jul. 26, 2016

(54) SEM SCANNER SENSING APPARATUS, SYSTEM AND METHODOLOGY FOR EARLY DETECTION OF ULCERS

(71) Applicants: THE REGENTS OF THE UNIVERSITY OF CALIFORNIA, Oakland, CA (US); BRUIN BIOMETRICS, LLC, Los Angeles, CA (US)

(72) Inventors: Majid Sarrafzadeh, Anaheim Hills, CA (US); William Kaiser, Los Angeles, CA (US); Alireza Mehrnia, Los Angeles, CA (US); Barbara M. Bates-Jensen, Pasadena, CA (US); Frank Wang, Cupertino, CA (US); Michael Flesch, Beverly Hills, CA (US); Joseph Boystak, Marina Del Rey, CA (US); Yeung Lam, Sherman Oaks, CA (US)

(73) Assignees: The Regents of the University of California, Oakland, CA (US); Bruin Biometrics, LLC, Los Angeles, CA (US)

(*) Notice: Subject to any disclaimer, the term of this patent is extended or adjusted under 35 U.S.C. 154(b) by 0 days.

(21) Appl. No.: 14/827,375

(22) Filed: Aug. 17, 2015

(65) Prior Publication Data
US 2015/0366499 A1 Dec. 24, 2015

Related U.S. Application Data

(63) Continuation of application No. 14/297,977, filed on Jun. 6, 2014, which is a continuation of application No.
(Continued)

(51) Int. Cl.
*A61B 5/00* (2006.01)
*A61B 5/053* (2006.01)
*A61B 5/05* (2006.01)

(52) U.S. Cl.
CPC . *A61B 5/443* (2013.01); *A61B 5/05* (2013.01); *A61B 5/0533* (2013.01); *A61B 5/445* (2013.01);
(Continued)

(58) Field of Classification Search
CPC ........ A61B 5/443; A61B 5/05; A61B 5/0533; A61B 5/445; A61B 2562/0214; A61B 2562/164; A61B 5/6843
See application file for complete search history.

(56) References Cited

U.S. PATENT DOCUMENTS 5,284,150 A * 2/1994 Butterfield ............. A61B 5/021
 600/485
6,330,479 B1 12/2001 Stauffer
(Continued)

FOREIGN PATENT DOCUMENTS

EP    1372475 B1   8/2009
WO   02080770 A1  10/2002
(Continued)

OTHER PUBLICATIONS

Korean Intellectual Property Office, International Search Report and Written Opinion issued on Feb. 9, 2012 for corresponding International Patent Application No. PCT/US2011/035618 (pp. 1-16), with claims searched (pp. 17-22).
(Continued)

*Primary Examiner* — Michael Kahelin
*Assistant Examiner* — Tho Tran
(74) *Attorney, Agent, or Firm* — David R. Marsh; Arnold & Porter LLP

(57) ABSTRACT

A handheld, conforming capacitive sensing apparatus configured to measure Sub-Epidermal Moisture (SEM) as a mean to detect and monitor the formation of pressure ulcers. The device incorporates an array of electrodes which are excited to measure and scan SEM in a programmable and multiplexed manner by a battery-less RF-powered chip. The scanning operation is initiated by an interrogator which excites a coil embedded in the apparatus and provides the needed energy burst to support the scanning/reading operation. Each electrode measures the equivalent sub-epidermal capacitance corresponding and representing the moisture content.

17 Claims, 18 Drawing Sheets

Related U.S. Application Data

13/668,047, filed on Nov. 2, 2012, now abandoned, which is a continuation of application No. PCT/US2011/035618, filed on May 6, 2011.

(60) Provisional application No. 61/332,755, filed on May 8, 2010, provisional application No. 61/453,852, filed on Mar. 17, 2011.

(52) U.S. Cl.
CPC ............... *A61B 5/447* (2013.01); *A61B 5/6843* (2013.01); *A61B 5/7271* (2013.01); *A61B 2562/0214* (2013.01); *A61B 2562/04* (2013.01); *A61B 2562/164* (2013.01)

(56) References Cited

U.S. PATENT DOCUMENTS

| | | | |
|---|---|---|---|
| 6,370,426 B1 * | 4/2002 | Campbell | A61B 5/442 324/696 |
| 7,783,344 B2 * | 8/2010 | Lackey | A61B 5/0537 600/547 |
| 2001/0051783 A1 * | 12/2001 | Edwards | A61B 18/1477 604/22 |
| 2002/0016535 A1 | 2/2002 | Martin et al. | |
| 2003/0036674 A1 | 2/2003 | Bouton | |
| 2003/0036713 A1 * | 2/2003 | Bouton | A61B 5/05 600/587 |
| 2004/0236200 A1 | 11/2004 | Say et al. | |
| 2004/0254457 A1 | 12/2004 | Van Der Weide | |
| 2005/0027175 A1 | 2/2005 | Yang | |
| 2005/0177061 A1 * | 8/2005 | Alanen | A61B 5/0531 600/547 |
| 2005/0245795 A1 | 11/2005 | Goode et al. | |
| 2008/0259577 A1 | 10/2008 | Hu et al. | |
| 2008/0278336 A1 * | 11/2008 | Ortega | A61B 5/1113 340/573.5 |
| 2010/0113979 A1 | 5/2010 | Sarrafzadeh et al. | |
| 2011/0301441 A1 | 12/2011 | Bandic et al. | |
| 2013/0041235 A1 | 2/2013 | Rogers et al. | |
| 2013/0123587 A1 | 5/2013 | Sarrafzadeh et al. | |
| 2013/0253285 A1 * | 9/2013 | Bly | A61B 5/4875 600/301 |
| 2014/0288397 A1 | 9/2014 | Sarrafzadeh et al. | |

FOREIGN PATENT DOCUMENTS

| | | |
|---|---|---|
| WO | 2004/105602 A1 | 12/2004 |
| WO | 2011/143071 A2 | 11/2011 |

OTHER PUBLICATIONS

Alanen, "Measurement of hydration in the stratum corneum with the Moisture Meter and comparison with the Corneometer", Skin Research and Technology 2004; 10: 32-37.
Allman et al, "Pressure ulcer risk factors among hospitalized patients with activity limitation," JAMA 273 (Mar. 15, 1995) 865-870.
Agency for Health Care Policy and Research (Rockville, Md: US Department of Health and Human Services), "Pressure ulcers in adults: Prediction and prevention," in Clinical Practice Guideline—Quick Reference Guide for Clinicians, May 1992, p. 117.
Thomas et al, "Hospital-acquired pressure ulcers and risk of death," Journal of the American Geriatrics Society 44 (Dec. 1996) 1435-1440.
Huang et al., (Apr. 29, 2008). A device for skin moisture and environment humidity detection. Sensors and Actuators B: Chemical pp. 206-212.
Lyder et al, "Quality of care for hospitalized Medicare patients at risk for pressure ulcers," Archives of Internal Medicine 161 (Jun. 25, 2001) 1549-1554.
O'Goshi, "Skin conductance; validation of Skicon-200EX compared to the original model, Skicon-100", Skin Research and Technology 2007; 13: 13-18.
"Recommended practices for positioning the patient in the preoperative practice setting," in Standards, Recommended Practices, and Guidelines (Denver: AORN, Inc, 2006) 587-592.
Jiricka et al, "Pressure ulcer risk factors in an ICU population," American Journal of Critical Care 4 (Sep. 1995) 361-367.
Dupont (2012). General Specifications for Kapton Polyimide Film. Retrieved from Dupont: http://www2.dupont.com/Kapton/en_US/assets/downloads/pdf/Gen_Specs.pdf, pp. 1-7.
Sewchuk et al. (Jul. 2006). Prevention and early detection of pressure ulcers in patients undergoing cardiac surgery. AORN Journal, vol. 84. No. 1, pp. 75-96.
Lee, (Jan. 5, 2007). CapSense Best Practices. Application Note 2394, pp. 1-10.
Dupont (2012) "Pyralux® FR Coverlay, Bondply & Sheet Adhesive," webpage, Retrieved from: www2.dupont.com/Pyralux/en_US/products/adhesives_films/FR/FR_films.html on Jun. 24, 2013, pp. 1-2.
Dupont (2012) "Pyralux® FR Copper-clad Laminate," webpage, Retrieved from: www2.dupont.com/Pyralux/en_US/products/laminate/FR/pyralux_fr.html on Jun. 24, 2013, pp. 1-2.
Australian Intellectual Property Office, Office Action issued on May 1, 2014 for corresponding Australian patent application No. 2011253253 (pp. 1-10) and pending claims (pp. 11-15) pp. 1-15.
Bates-Jensen et al. "Subepidermal moisture differentiates erythema and stage I pressure ulcers in nursing home residents," Wound Repair and Regeneration vol. 16 (2008) pp. 189-197.
Nuutinen et al. "Validation of a new dielectric device to asses changes of tissue water in skin and subcutaneous fat," Physiological Measurement vol. 25 (2004) pp. 447-454.
European Patent Office, ESSR issued on Aug. 22, 2014 for corresponding European Patent Application No. 117811061.4 (pp. 1-7) and pending claims (pp. 3-10) pp. 1-10.
Australian Patent Office, Office Action issued on Jun. 1, 2015, for corresponding Australian Patent Application No. 2011253253 (pp. 1-4) and claims (pp. 5-10) pp. 1-10.
Barnes, "Moisture Meters for Use on Thin Lumber and Veneers", 1956, Moisture Register Co., pp. 1-5.
European Patent Office, Office Action issued on Jul. 13, 2015, for corresponding European Patent Application No. 11781061.4 (pp. 1-5) and claims (pp. 6-9) pp. 1-9.
Swisher SL, Lin MC, Liao A, Leeflang EJ, Khan Y, Pavinatto FJ, Mann K, Naujokas A, Young D, Roy S, Harrison MR, Arias AC, Subramanian V, Maharbiz MM. Impedance sensing device enables early detection of pressure ulcers in vivo. Nat Commun 2015;6:6575.
Valentinuzzi ME, Morucci JP, Felice CJ. Bioelectrical impedance techniques in medicine. Part II: Monitoring of physiological events by impedance. Crit Rev Biomed Eng 1996;24(4-6):353-466.
Vangilder C, MacFarlane GD, Meyer S. Results of nine international pressure ulcer prevalence surveys: 1989 to 2005. Ostomy Wound Manage 2008;54(2):40-54.
Wagner DR, Jeter KF, Tintle T, Martin MS, Long JM 3rd. Bioelectrical impedance as a discriminator of pressure ulcer risk. Adv Wound Care 1996;9(2):30-7.
Watanabe R1, Kotoura H, Morishita Y. CT analysis of the use of the electrical impedance technique to estimate local oedema in the extremities in patients with lymphatic obstruction. Med Biol Eng Comput 1998;36(1):60-5.
Weiss SJ. Tissue destruction by neutrophils. N Engl J Med 1989;320(6):365-76.
Alberts B, Johnson A, Lewis J, Raff M, Roberts K, Walter P. Cell junctions, cell adhesion, and the extracellular matrix. In: Molecular Biology of the Cell. New York, NY: Garland Science, 2002:1065-1125.
Arao H, Obata M, Shimada T, Hagisawa S. Morphological characteristics of the dermal papillae in the development of pressure sores. J Tissue Viability 1998;8(3):17-23.
Bader DL, Barnhill RL, Ryan TJ. Effect of externally applied skin surface forces on tissue and vasculature. Arch Phys Med Rehabil 1986;67(11):807-11.
Bates-Jensen BM, McCreath HE, Kono A, Apeles NC, Alessi C. Subepidermal moisture predicts erythema and stage 1 pressure ulcers in nursing home residents: a pilot study. J Am Geriatr Soc 2007;55(8):1199-205.

(56) References Cited

OTHER PUBLICATIONS

Bates-Jensen BM, McCreath HE, Pongquan V, Apeles NC. Subepidermal moisture differentiates erythema and stage I pressure ulcers in nursing home residents. Wound Repair Regen 2008;16(2):189-97.

Bates-Jensen BM, McCreath HE, Pongquan V. Subepidermal Moisture is Associated With Early Pressure Ulcer Damage in Nursing Home Residents With Dark Skin Tones. Pilot Findings. J Wound Ostomy Continence Nurs 2009;36(3):277-84.

Bergstrand S, Källman U, EK AC, Lindberg LG, Engström M, Sjoberg F, Lindgren M. Pressure-induced vasodilation and reactive hyperemia at different depths in sacral tissue under clinically relevant conditions. Microcirculation 2014;21(8):761-71.

Brem H, Maggi J, Nierman D, Rolnitzky L, Bell D, Rennert R, Golinko M, Yan A, Lyder C, Vladeck B. High cost of stage IV pressure ulcers. Am J Surg 2010;200(4):473-7.

Brienza D, Antokal S, Herbe L, Logan S, Maguire J, Van Ranst J, Siddiqui A. Friction-induced skin injuries—are they pressure ulcers? An updated NPrUAP white paper. J Wound Ostomy Continence Nurs. 2015;42 (1):62-4.

Carmo-Araújo EM, Dal-Pai-Silva M, Dal-Pai V, Cecchini R, Anjos Ferreira AL. Ischaemia and reperfusion effects on skeletal muscle tissue: morphological and histochemical studies. Int J Exp Pathol 2007;88 (3):147-54.

Ceelen KK, Stekelenburg A, Loerakker S, Strijkers GJ, Bader DL, Nicolay K, Baaijens FP, Oomens CW. Compression-induced damage and internal tissue strains are related. J Biomech 2008;41 (16):3399-404.

Ching CT, Chou MY, Jiang SJ, Huang SH, Sun TP, Liu WH, Liu CM. Tissue electrical properties monitoring for the prevention of pressure sore. Prosthet Orthot Int 2011;35(4):386-94.

Clendenin M, Jaradeh K, Shamirian A, Rhodes SL. Inter-operator and inter-device agreement and reliability of the SEM Scanner. J Tissue Viability 2015;24(1):17-23.

De Lorenzo A, Andreoli A, Matthie J, Withers P. Predicting body cell mass with bioimpedance by using theoretical methods: a technological review. J Appl Physiol 1997;82(5):1542-58.

Demarre L, Van Lancker A, Verhaeghe S, Van Hecke A, Grypdonck M, Lemey J, Annemans L, Beeckman D. The cost of prevention and treatment of pressure ulcers: a systematic review. Int J Nurs Stud. 2015 [in press].

Dodde RE, Bull JL, Shih AJ. Bioimpedance of soft tissue under compression. Physiol Meas. 2012;33(6):1095-109.

Eberlein-Gonska M, Petzold T, Helaβ G, Albrecht DM, Schmitt J. The incidence and determinants of decubitus ulcers in hospital care: an analysis of routine quality management data at a university hospital. Dtsch Arztebl Int. Aug. 2013;110(33-34):550-6.

Gabriel C. 1996. Compilation of the Dielectric Properties of Body Tissues at Rf and Microwave Frequencies, Report N.AL/OE-TR-1996-0037, Occupational and Environmental Health Directorate, Radiofrequency Radiation Division, Brooks Air Force Base, TX. Available at: www.dtic.mil/dtic/tr/fulltext/u2/a305826.pdf.

Gabriel S, Lau RW, Gabriel C. The dielectric properties of biological tissues: II. Measurements in the frequency range 10 Hz to 20 GHz. Phys Med Biol 1996;41(11):2251-69.

Gardiner JC, Reed PL, Bonner JD, Haggerty DK, Hale DG. Incidence of hospital-acquired pressure ulcers—a population-based cohort study. Int Wound J Dec. 3, 2014. [epub ahead of print] doi: 10.1111/iwj.12386.

Gershon S, Okonkwo H, Rhodes S, Burns M. SEM Scanner readings to assess pressure induced tissue damage. 17th Annual European Pressure Ulcer Advisory Panel (EPUAP) meeting, Stockholm, Sweden, Aug. 27-29, 2014.

González-Correa CA, Brown BH, Smallwood RH, Walker DC, Bardhan KD. Electrical bioimpedance readings increase with higher pressure applied to the measuring probe. Physiol Meas 2005;26(2):539-47.

Guihan M, Bates-Jenson BM, Chun S, Parachuri R, Chin AS, McCreath H. Assessing the feasibility of subepidermal moisture to predict erythema and stage 1 pressure ulcers in persons with spinal cord injury: a pilot study. J Spinal Cord Med 2012;35(1):46-52.

Harrow JJ, Mayrovitz HN. Subepidermal moisture surrounding pressure ulcers in persons with a spinal cord injury: A pilot study. J Spinal Cord Med 2014;37(6):719-28.

Houwing R1, Overgoor M, Kon M, Jansen G, Van Asbeck BS, Haalboom JR. Pressure-induced skin lesions in pigs: reperfusion injury and the effects of vitamin E. J Wound Care 2000;9(1):36-40.

Jan YK, Lee B, Liao F, Foreman RD. Local cooling reduces skin ischemia under surface pressure in rats: an assessment by wavelet analysis of laser Doppler blood flow oscillations. Physiol Meas 2012;33(10):1733-45.

Jiang L, Dai Y, Cui F, Pan Y, Zhang H, Xiao J, Xiaobing FU. Expression of cytokines, growth factors and apoptosis-related signal molecules in chronic pressure ulcer wounds healing. Spinal Cord 2014;52(2):145-51.

Jiang LP, Tu Q, Wang Y, Zhang E. Ischemia-reperfusion injury-induced histological changes affecting early stage pressure ulcer development in a rat model. Ostomy Wound Manage. 2011;57(2):55-60.

Kanai H, Haeno M, Sakamoto K. Electrical measurement of fluid distribution in legs and arms. Med Prog Technol 1987;12(3-4):159-70.

Kasuya A, Sakabe J, Tokura Y. Potential application of in vivo imaging of impaired lymphatic duct to evaluate the severity of pressure ulcer in mouse model. Sci Rep. 2014:25;4:4173.

Loerakker S, Manders E, Strijkers GJ, Nicolay K, Baaijens FP, Bader DL, Oomens CW. The effects of deformation, ischemia, and reperfusion on the development of muscle damage during prolonged loading. J Appl Physiol 2011;111(4):1168-77.

Loerakker S, Stekelenburg A, Strijkers GJ, Rijpkema JJ, Baaijens FP, Bader DL, Nicolay K, Oomens CW. Temporal effects of mechanical loading on deformation-induced damage in skeletal muscle tissue. Ann Biomed Eng 2010;38(8):2577-87.

Martinsen O, Grimnes S. Bioimpedance and Bioelectricity Basics, Oxford, UK: Elsevier Academic Press, 2011: Chapters 1 and 10.

Mathiesen AS, Nørgaard K, Andersen MF, Møller KM, Ehlers LH. Are labour-intensive efforts to prevent pressure ulcers cost-effective? J Med Econ 2013;16(10):1238-45.

Matthie J, Zarowitz B, De Lorenzo A, Andreoli A, Katzarski K, Pan G, Withers P. Analytic assessment of the various bioimpedance methods used to estimate body water. J Appl Physiol 1998;84(5):1801-16.

Miller GE, Seale J. Lymphatic clearance during compressive loading. Lymphology. 1981;14(4):161-6.

Moore Z, Cowman S, Conroy RM. A randomised controlled clinical trial of repositioning, using the 30° tilt, for the prevention of pressure ulcers. J Clin Nurs 2011;20(17-18):2633-44.

Moore Z, Cowman S. Pressure ulcer prevalence and prevention practices in care of the older person in the Republic of Ireland. J Clin Nurs 2012;21:362-71.

Moore Z, Johanssen E, Van Etten M. A review of PU prevalence and incidence across Scandinavia, Iceland and Ireland (Part I). J Wound Care 2013;22(7):361-2, 364-8.

Mulasi U, Kuchnia AJ, Cole AJ, Earthman CP. Bioimpedance at the Bedside: Current Applications, Limitations, and Opportunities. Nutr Clin Pract 2015;30(2):180-93.

National Pressure Ulcer Advisory Panel, European Pressure Ulcer Advisory Panel, Pan Pacific Pressure Injury Alliance. Prevention and Treatment of Pressure Ulcers: Clinical Practice Guideline. Haesler E, editor. Osborne Park, Western Australia: Cambridge Media, 2014.

Nixon J, Cranny G, Bond S. Pathology, diagnosis, and classification of pressure ulcers: comparing clinical and imaging techniques. Wound Repair Regen 2005;13(4):365-72.

Oomens CW, Bader DL, Loerakker S, Baaijens F. Pressure Induced Deep Tissue Injury Explained. Ann Biomed Eng 2015;43(2):297-305.

Scallan J, Huxley VH, Korthuis RJ. Capillary fluid exchange: regulation, functions, and pathology. San Rafael, CA: Morgan & Claypool Life Sciences, 2010: Chapter 4.

Schultz G, Ladwig G, Wysocki A. Extracellular matrix: review of its role in acute and chronic wounds. World Wide Wounds 2005.

(56) References Cited

OTHER PUBLICATIONS

Accessed on Jun. 16, 2015. Available at http://www.worldwidewounds.com/2005/august/Schultz/Extrace-Matric-Acute-Chronic-Wounds.html.

Schwan HP. Electrical properties of tissue and cell suspensions. Adv Biol Med Phys 1957;5:147-209.

Sener G, Sert G, Ozer Sehirli A, Arbak S, Uslu B, Gedik N, Ayanoglu-Dulger G. Pressure ulcer-induced oxidative organ injury is ameliorated by beta-glucan treatment in rats. Int Immunopharmacol 2006;6(5):724-32.

Sprigle S, Linden M, Riordan B. Analysis of localized erythema using clinical indicators and spectroscopy. Ostomy Wound Manage 2003;49(3):42-52.

Stekelenburg A, Gawlitta D, Bader DL, Oomens CW. Deep tissue injury: how deep is our understanding? Arch Phys Med Rehabil 2008;89(7):1410-3.

Stekelenburg A, Strijkers GJ, Parusel H, Bader DL, Nicolay K, Oomens CW. Role of ischemia and deformation in the onset of compression-induced deep tissue injury: MRI-based studies in a rat model. J Appl Physiol 2007;102(5):2002-11.

\* cited by examiner

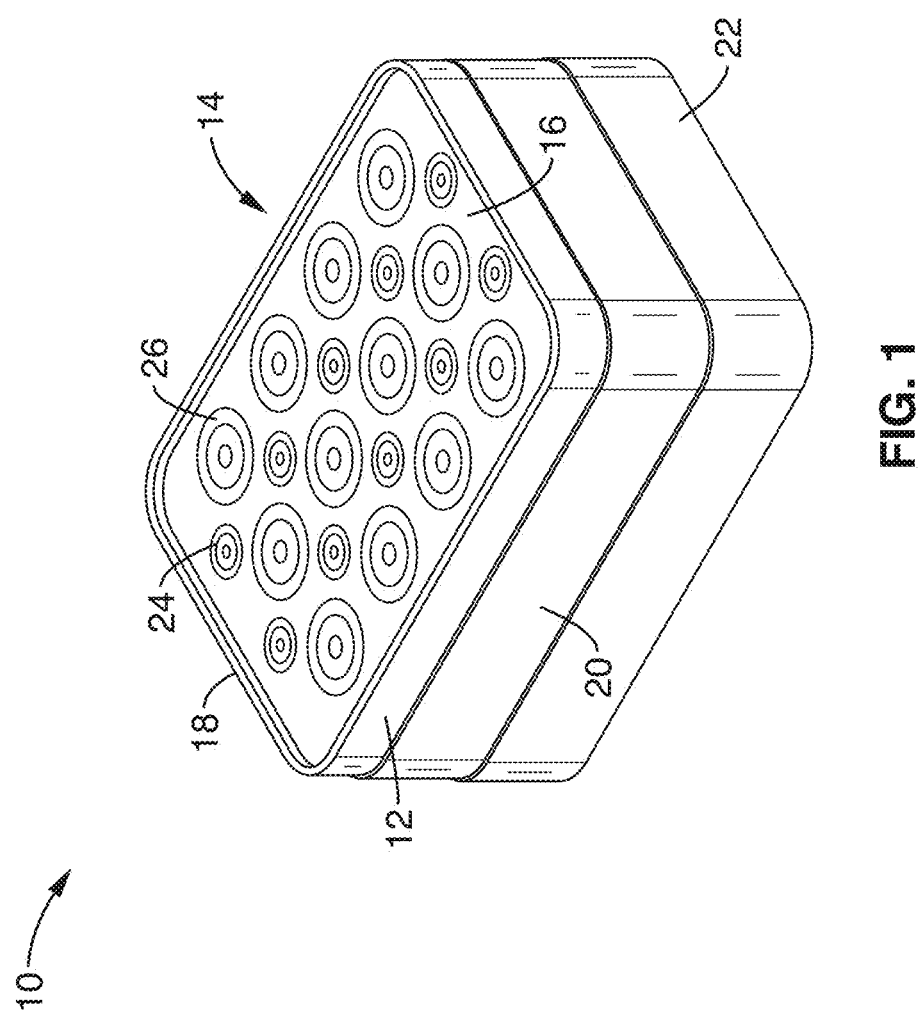

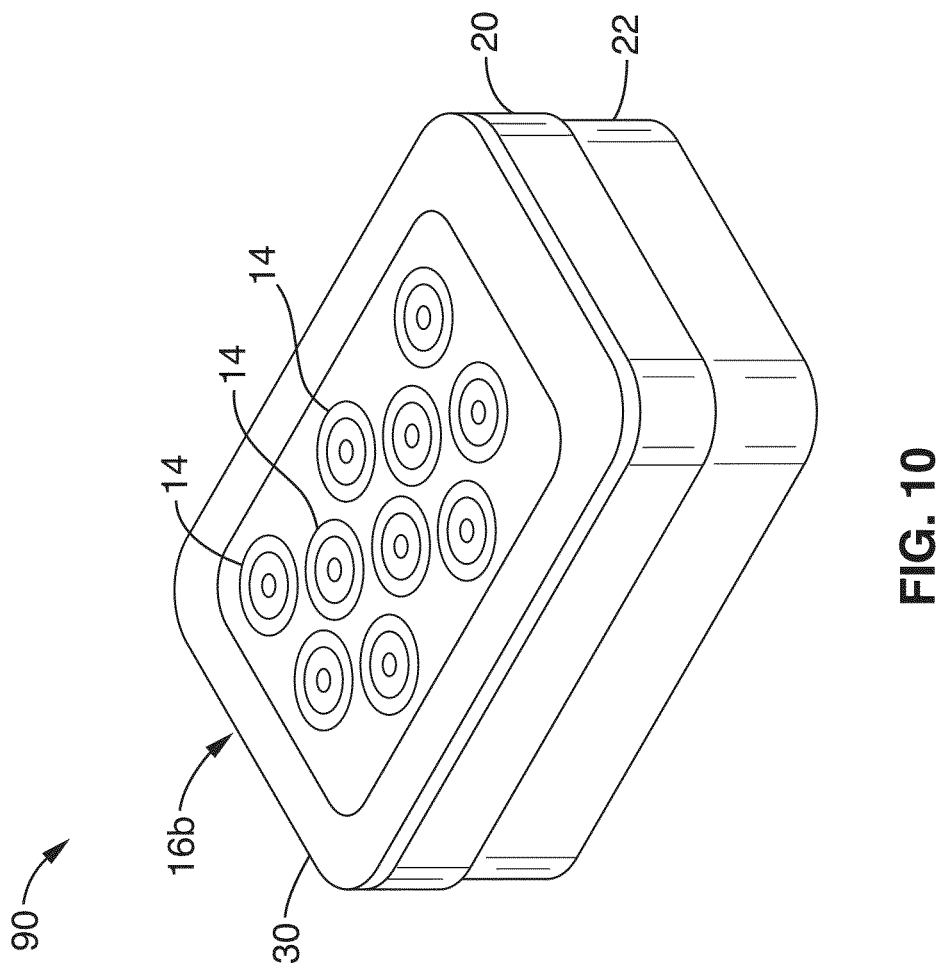

SEM SCANNER SENSING APPARATUS, SYSTEM AND METHODOLOGY FOR EARLY DETECTION OF ULCERS

CROSS-REFERENCE TO RELATED APPLICATIONS

This application is a continuation of U.S. patent application Ser. No. 14/297,977 filed on Jun. 6, 2014, incorporated herein by reference in its entirety, which is a continuation of U.S. patent application Ser. No. 13/668,047 filed on Nov. 2, 2012, incorporated herein by reference in its entirety, which is a 35 U.S.C. §111(a) continuation of PCT international application number PCT/US2011/035618 filed on May 6, 2011, incorporated herein by reference in its entirety, which claims the benefit of U.S. provisional patent application Ser. No. 61/332,755 filed on May 8, 2010, incorporated herein by reference in its entirety, and which claims the benefit of U.S. provisional patent application Ser. No. 61/453,852 filed on Mar. 17, 2011, incorporated herein by reference in its entirety. Priority is claimed to each of the foregoing applications.

The above-referenced PCT international application was published as PCT International Publication No. WO 2011/143071 on Nov. 17, 2011 and republished on Apr. 5, 2012, and is incorporated herein by reference in its entirety.

STATEMENT REGARDING FEDERALLY SPONSORED RESEARCH OR DEVELOPMENT

Not Applicable

INCORPORATION-BY-REFERENCE OF COMPUTER PROGRAM APPENDIX

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. §1.14.

BACKGROUND OF THE INVENTION

1. Field of the Invention

This invention pertains generally to monitoring skin pressure ulcers and more particularly to skin ulcer monitoring via measurement of Sub-epidermal Moisture (SEM).

2. Description of Related Art

Patients' skin integrity has long been an issue of concern for nurses and in nursing homes. Maintenance of skin integrity has been identified by the American Nurses Association as an important indicator of quality nursing care. Meanwhile, pressure ulcers remain a major health problem particularly for hospitalized older adults. When age is considered along with other risk factors, the incidence of pressure ulcers is significantly increased. Overall incidence of pressure ulcers for hospitalized patients ranges from 2.7% to 29.5%, and rates of greater than 50% have been reported for patients in intensive care settings. In a multicenter cohort retrospective study of 1,803 older adults discharged from acute care hospitals with selected diagnoses, 13.2% (i.e., 164 patients) demonstrated an incidence of stage I ulcers. Of those 164 patients, 38 (16%) had ulcers that progressed to a more advanced stage. Pressure ulcers additionally have been associated with an increased risk of death one year after hospital discharge. The estimated cost of treating pressure ulcers ranges from $5,000 to $40,000 for each ulcer, depending on severity.

Therefore, there is an urgent need to develop a preventive solution to measure moisture content of the skin as a mean to detect early symptoms of ulcer development.

BRIEF SUMMARY OF THE INVENTION

An aspect of the present invention is a smart compact capacitive sensing conforming handheld apparatus configured to measure Sub-epidermal Moisture (SEM) as a mean to detect and monitor the development of pressure ulcers. The device incorporates an array of electrodes which are excited to measure and scan SEM in a programmable and multiplexed manner by a battery-less RF-powered chip. The scanning operation is initiated by an interrogator which excites a coil embedded in the apparatus and provides the needed energy burst to support the scanning/reading operation. Each embedded electrode measures the equivalent sub-epidermal capacitance corresponding and representing the moisture content of the target surface.

An aspect of this invention is the in situ sensing and monitoring of skin or wound or ulcer development status using a wireless, biocompatible RF powered capacitive sensing system referred to as smart SEM imager. The present invention enables the realization of smart preventive measures by enabling early detection of ulcer formation or inflammatory pressure which would otherwise have not been detected for an extended period with increased risk of infection and higher stage ulcer development.

In one beneficial embodiment, the handheld capacitive sensing imager apparatus incorporates pressure sensing components in conjunction with the sensing electrodes to monitor the level of applied pressure on each electrode in order to guarantee precise wound or skin electrical capacitance measurements to characterize moisture content. In summary, such embodiment would enable new capabilities including but not limited to: 1) measurement capabilities such as SEM imaging and SEM depth imaging determined by electrode geometry and dielectrics, and 2) signal processing and pattern recognition having automatic and assured registration exploiting pressure imaging and automatic assurance of usage exploiting software systems providing usage tracking.

One major implication of this sensor-enhanced paradigm is the ability to better manage each individual patient resulting in a timelier and more efficient practice in hospitals and even nursing homes. This is applicable to patients with a history of chronic wounds, diabetic foot ulcers, pressure ulcers or post-operative wounds. In addition, alterations in signal content may be integrated with the activity level of the patient, the position of patient's body and standardized assessments of symptoms. By maintaining the data collected in these patients in a signal database, pattern classification, search, and pattern matching algorithms can be developed to better map symptoms with alterations in skin characteristics and ulcer development. This approach is not limited to the specific condition of ulcer or wound, but may have broad application in all forms of wound management and even skin diseases or treatments.

One aspect is apparatus for sensing sub-epidermal moisture (SEM) from a location external to a patient's skin. The apparatus includes a bipolar RF sensor embedded on a flexible substrate, and a conformal pressure pad disposed adjacent and underneath the substrate, wherein the conformal pressure pad is configured to support the flexible substrate while allowing the flexible substrate to conform to a non-planar sensing surface of the patient's skin. The apparatus further includes interface electronics coupled to the sensor; wherein the interface electronics are configured to control emission and reception of RF energy to interrogate the patient's skin.

Another aspect is a method for monitoring the formation of pressure ulcers at a target location of a patient's skin. The method includes the steps of positioning a flexible substrate adjacent the target location of the patient's skin; the flexible substrate comprising one or more bipolar RF sensors; conforming the flexible substrate to the patient's skin at the target location; exciting the one or more bipolar RF sensor to emit RF energy into the patient's skin; and measuring the capacitance of the skin at the target location as an indicator of the Sub-Epidermal Moisture (SEM) at the target location.

Further aspects of the invention will be brought out in the following portions of the specification, wherein the detailed description is for the purpose of fully disclosing preferred embodiments of the invention without placing limitations thereon.

BRIEF DESCRIPTION OF THE SEVERAL VIEWS OF THE DRAWING(S)

The invention will be more fully understood by reference to the following drawings which are for illustrative purposes only:

FIG. 1 illustrates an assembled perspective component view of the SEM Scanner of the present invention.

FIG. 10 illustrates a perspective view of an assembled SEM scanner with an alternative array of sensors in accordance with the present invention.

DETAILED DESCRIPTION OF THE INVENTION

In one exemplary embodiment, a smart handheld capacitive sensing device according to the present invention employs a programmable sensing electrode array. This is based on methods that use an interrogator to excite the embedded electrodes.

Figure 7:
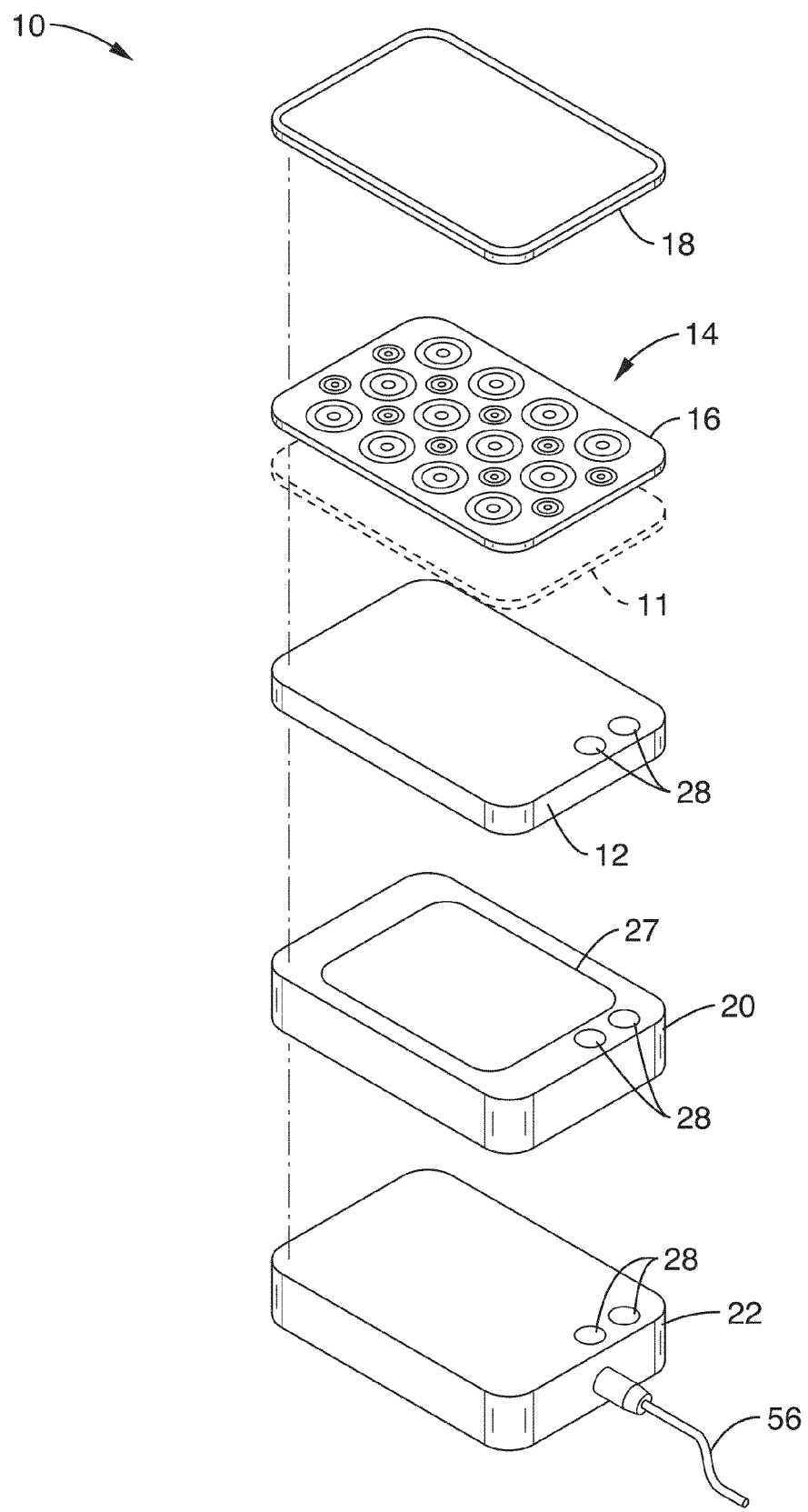
FIG. 7 illustrates an exploded perspective component view of the SEM scanner of FIG. 1.

FIG. 1 and FIG. 7 illustrate an SEM scanning/sensing apparatus 10 according to the present invention. The apparatus 10 comprises five main components, including a top silicone edge sealing gasket 18 encircling a Kapton-based sensing substrate 16, which rests on a conformal silicone pressure pad 12. A thick annular silicone spacer 20 is disposed under the pressure pad to provide free space for the pressure pad to deform. The bottom layer comprises an interface electronics package enclosure 22 that houses interface circuitry for interrogating and transmitting data for evaluation. These five main components are described in further detail below.

In the embodiment shown in FIG. 1, an array 14 of individual RF electrode sensors 24 and 26 is embedded on a flexible biocompatible substrate 16. Substrate 16 may comprise a laminated Kapton (Polyimide) chip-on-flex.

Figure 2:
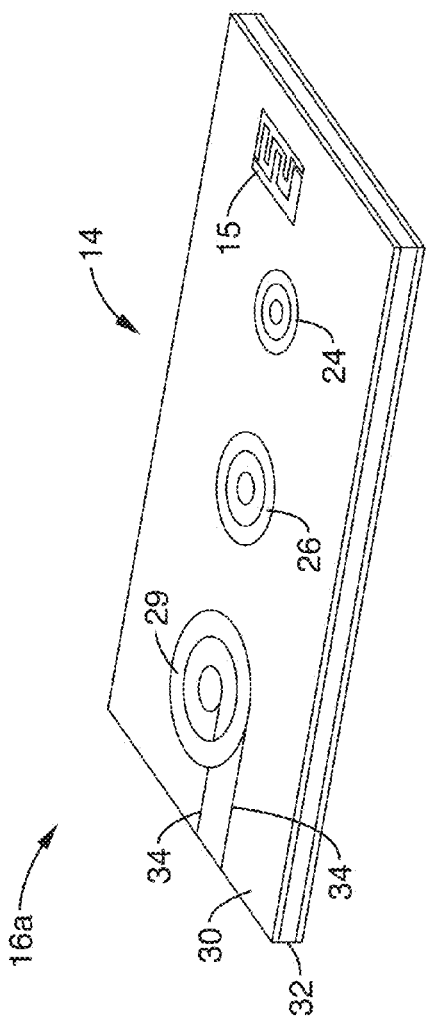
FIG. 2 illustrates a perspective view of a Kapton-based conforming sensing substrate assembly of the present invention.

FIG. 2 illustrates one embodiment of a Kapton sensor substrate 16a that comprises an array 14 of differing sized concentric sensing electrodes. A flexible biocompatible Polyimide or Kapton substrate 32 comprises a layer of sensing electrodes coated on one side with an ultra thin cover layer 30 of Polyimide (e.g. CA335) to isolate the electrodes from direct moisture contact and also to provide a uniform contact surface.

In FIG. 2, sample capacitive sensing electrodes of different sizes (e.g. 24, 26, and 29) are shown in an array 14, and which are manipulated to achieve and sense different depths of skin. The array of sensing electrodes 14 may comprise any number of different shape and configurations, such as the concentric circles 24, 26, 29, or the interdigitating fingers of sensor 15.

Figure 3:
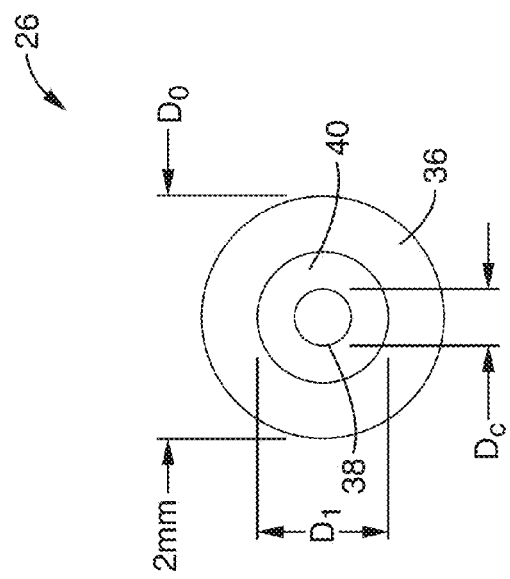
FIG. 3 shows a top view of an exemplary concentric sensing electrode in accordance with the present invention.

FIG. 3 illustrates a close-up top view of a concentric sensing pad 26 in accordance with the present invention. Pad 26 comprises a bipolar configuration having a first electrode 36 comprising an outer annular ring disposed around a second inner circular electrode 38. Outer ring electrode 36 has an outer diameter $D_o$ and an inner diameter $D_i$ that is larger than the diameter $D_c$ of the circular inner electrode 38 to form annular gap 40. Inner circular electrode 38 and outer ring electrode 36 are coupled electrically to interface electronics in the interface electronics package 22. As shown in greater detail in FIGS. 4 and 5, electrodes 36 and 38 are disposed on separate layers within the substrate assembly 16.

The dimensions of the sensor pads 24, 26 generally correspond to the depth of interrogation into the derma of the patient. Accordingly, a larger diameter pad (e.g. pad 26 or 29) will penetrate deeper into the skin than a smaller pad. The desired depth may vary depending on the region of the body being scanned, or the age, skin anatomy or other characteristic of the patient. Thus, SEM scanner 10 may comprise an array of different sized pads (e.g. small pads 24 and medium sized pads 26 shown in FIG. 1) each individually coupled to the interface electronics package 22.

Figure 4:
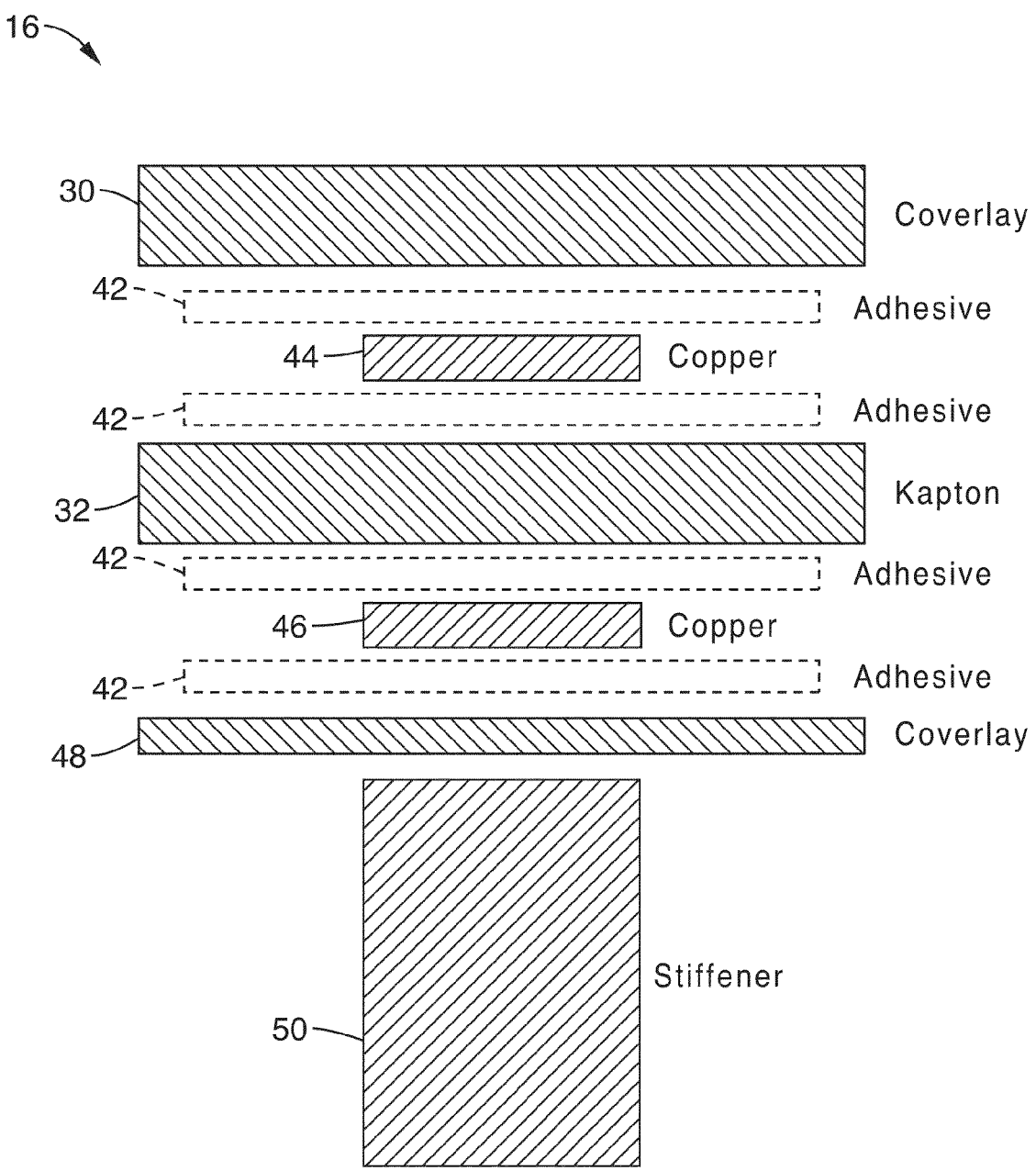
FIG. 4 illustrates a side view of a flex stack-up for the Kapton-based conforming sensing substrate shown in FIG. 2.

FIG. 4 illustrates side view of a flex stack-up for a Kapton based substrate assembly 16, where thin adhesive layers 42 are used to attach a Kapton layer 32 in between copper layers 44 and 46, all of which are disposed between upper coverlay 30 and lower coverlay 48. A stiffener 50 is disposed under lower coverlay 48, being positioned directly under copper layer 46 of the sensing pads. The stiffener 50 forms a rigid portion of the substrate where sensing pad array 14, connectors (e.g. connectors 66, 76, or 86 shown in FIG. 6) and interfacing (e.g. lead wires 34) are located, so that these areas do not deform, whereas the rest of the substrate is free to deform. The top copper layer 44 is used to etch out electrode array 14 and corresponding copper routing 34 to the connectors. The bottom copper layer 46 preferably comprises a crisscross ground plane to shield electrode array 14 from unwanted electromagnetic interference.

In one embodiment, the flex substrate 16 assembly comprises Pyralux FR material from Dupont. In an exemplary configuration, approximately 5 mil thick FR9150R double-sided Pyralux FR copper clad laminate is used as the Kapton substrate. Top coverlay 30 comprises Pyralux 5 mil FR0150 and the bottom coverlay 48 comprises 1 mil FR0110 Pyralux. The thickness of the top FR0150 coverlay 30 is an important parameter as it affects the sensitivity of sensing electrodes in measuring skin moisture content. Copper layers 44, 46 are generally 1.4 mil thick, while adhesive layers 42 are generally 1 mil thick. The stiffener 50 is shown in FIG. 4 is approximately 31 mil thick.

Figure 5:
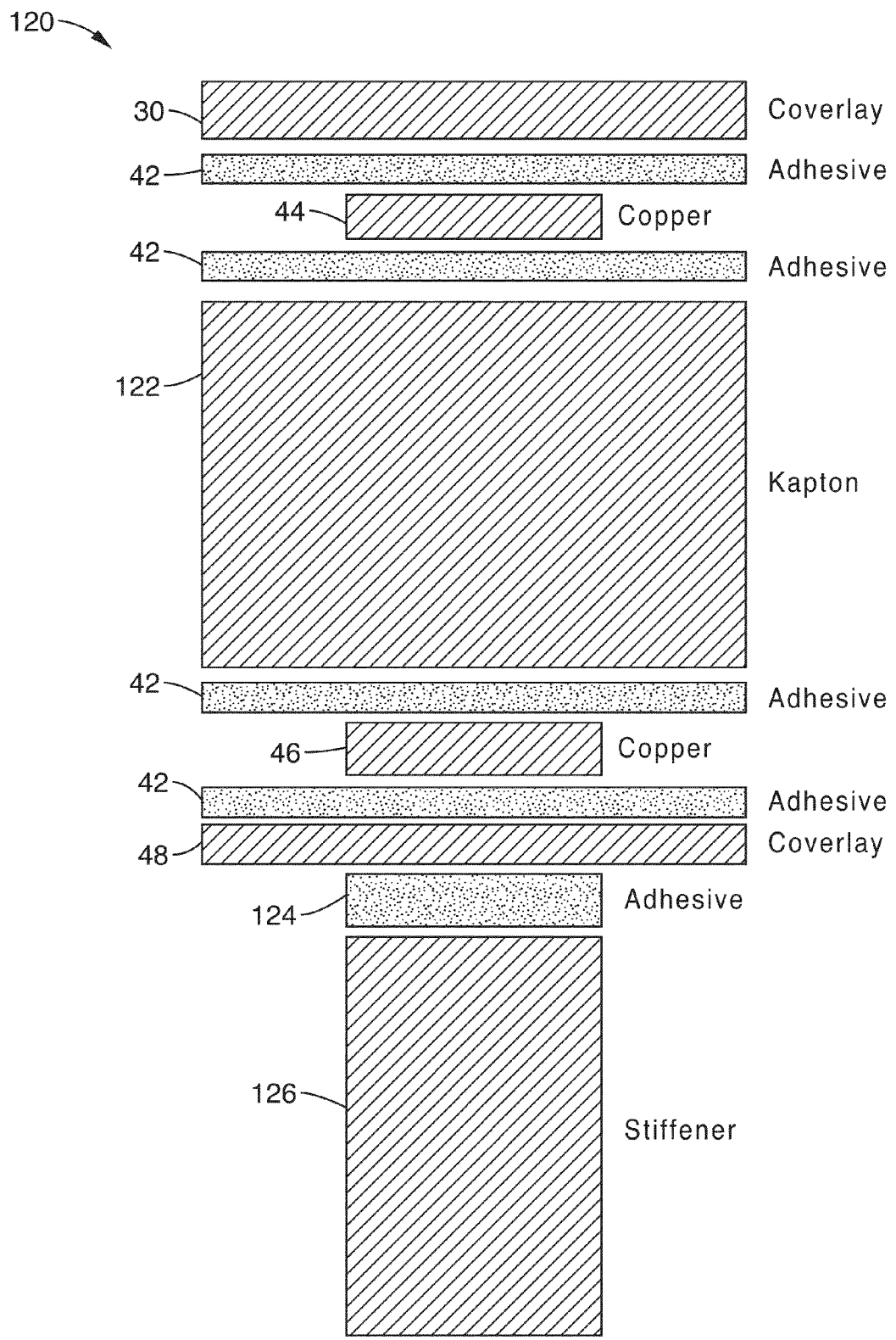
FIG. 5 illustrates a side view of an alternative flex stack-up for a Kapton-based conforming sensing substrate.

FIG. 5 shows a side view of a preferred alternative flex stack-up for a Kapton based substrate 120, where thin adhesive layers 42 (1 mil) are used to attach an 18 mil Kapton layer 122 in between 1.4 mil copper layers 44 and 46, all of which are disposed between 2 mil upper coverlay 30 and 1 mil lower coverlay 48. A stiffener 50 is disposed under lower coverlay 48, being positioned directly under copper layer 46 of the sensing pad. The 31 mil FR4 stiffener 126 forms a rigid portion of the substrate under the array 14 of sensing pads, connectors 66 and interfacing 34. A 2 mil layer of PSA adhesive 124 is used between the bottom coverlay 48 and stiffener 126. The layering of assembly 120 is configured to provide proper shielding from interference.

Figure 6:
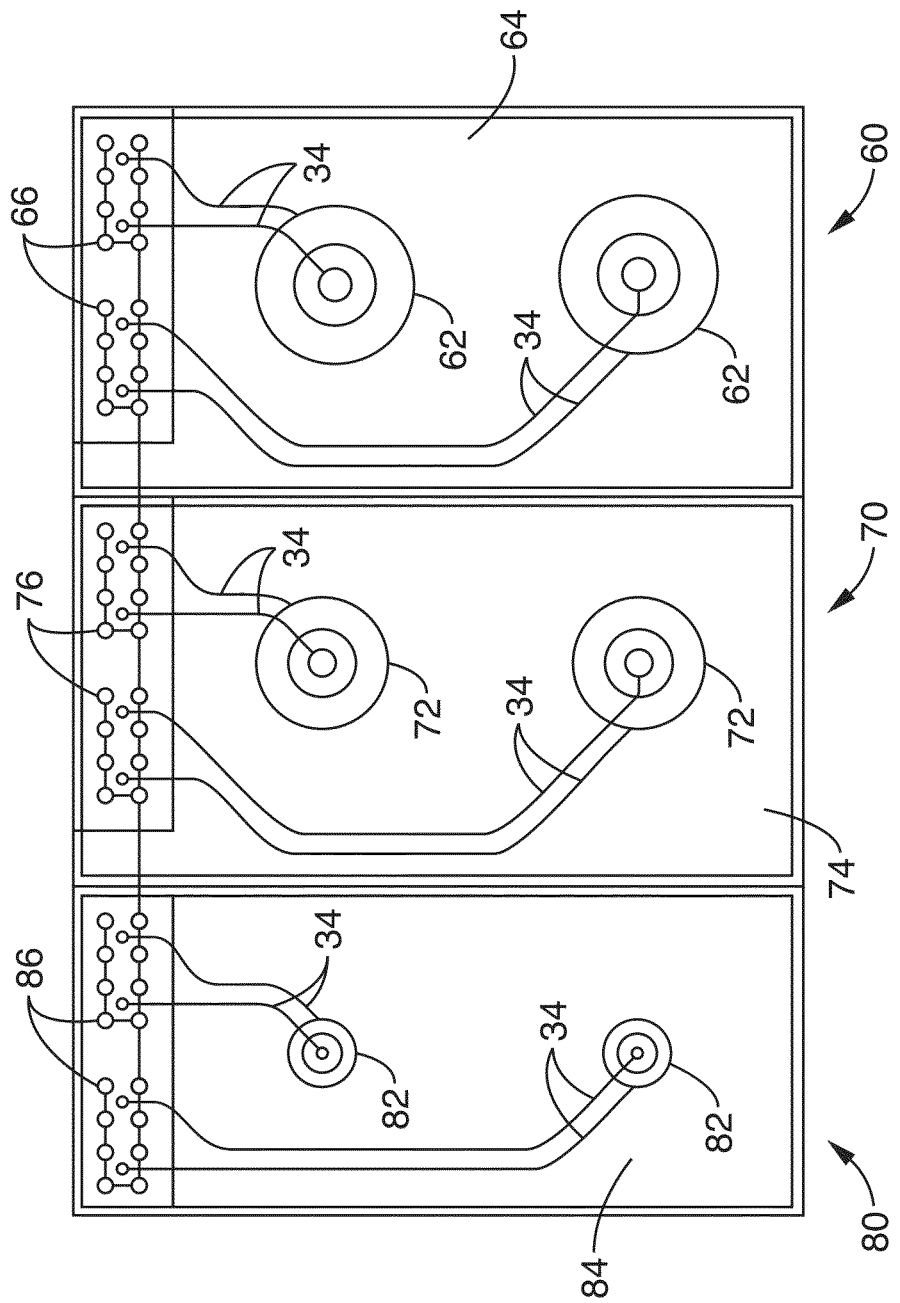
FIG. 6 shows a top view of two-electrode sensing Kapton-based flex sensor substrates for three alternative types of capacitive sensing concentric electrodes.

FIG. 6 shows a top view of three separate and adjacently arranged concentric bipolar electrode sensing Kapton-based flex pads 60, 70 and 80 having different sized capacitive sensing concentric electrodes. Pad 60 comprises a substrate having two large concentric electrodes 62 wired through substrate 64 via connectors 34 to lead line inputs 66. Pad 70 comprises a substrate having two medium concentric electrodes 72 wired through substrate 74 to lead line inputs 76. Pad 80 comprises a substrate having two small concentric electrodes 82 wired through substrate 84 to lead line inputs 86. The configuration shown in FIG. 6 is optimized for cutting/manufacturing and also to avoid interference between data lines and sensors. Each of the bipolar electrode pads is individually wired to the electronics package 22 to allow for independent interrogation, excitation, and data retrieval.

FIG. 7 illustrates an exploded perspective component view of the SEM scanner 10. The silicone edge sealing gasket 18 is applied over the Kapton sensor substrate assembly 16 to seal and shield the edge interface connectors through which interface electronics package 22 excite and controls the sensing electrode array 14. The Kapton sensor substrate assembly 16 rests on a conformal silicone pressure pad 12 that provides both support and conformity to enable measurements over body curvature and bony prominences.

In one beneficial embodiment, pressure sensor 11 may be embedded under each sensing electrode 24, 26 (e.g. in an identical array not shown), sandwiched between Kapton sensor substrate 26 and the conformal silicone pressure pad 28 to measure applied pressure at each electrode, thus ensuring a uniform pressure and precise capacitance sensing.

Lead access apertures 28 provide passage for routing the connector wires (not shown) from the substrate connectors (e.g. 66, 76, 86) through the pressure pad 12, annular spacer 20 to the interface electronics 22.

The annular silicone spacer 20 comprises a central opening 27 that provides needed spacing between the conformal silicone pressure pad 12 and the interface electronics package 22 to allow the pressure pad 12 and flexible substrate to conform in a non-planar fashion to conduct measurements over body curvatures or bony prominences.

In one embodiment, the interface electronics package 22 is connected to a logging unit or other electronics (not shown) through wire-line USB connector 56.

The interface electronics package 22 preferably comprises an enclosure that contains all the electronics (not shown) needed to excite, program and control the sensing operation and manage the logged data. The electronics package 22 may also comprise Bluetooth or other wireless communication capabilities to allow for transfer of sensing data to a computer or other remote device. Docked data transfer is also contemplated, in addition to real-time Bluetooth transfer. A gateway device (not shown) may be used for communicating with the SEM device 10 and data formatting prior to upload to a computer or backend server.

Figure 8:
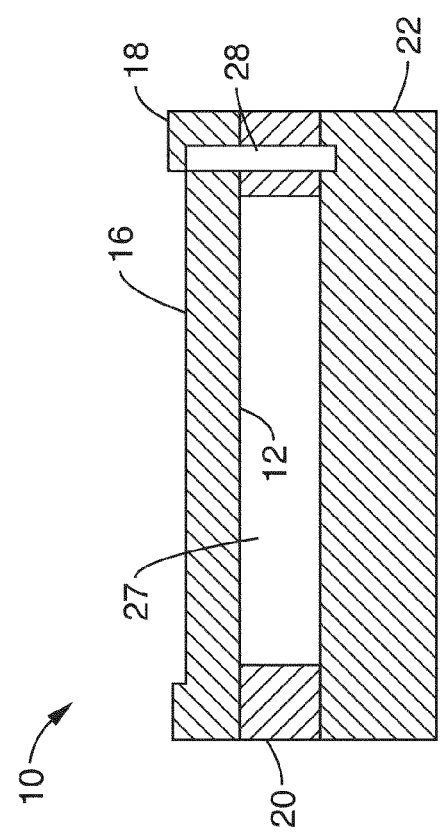
FIG. 8 illustrates a schematic side view of the SEM scanner of FIG. 1.

FIG. 8 is a schematic side view of the SEM scanner 10 in the nominal configuration, showing the edge gasket 18 over Kapton substrate 16, and lead access apertures 28, which provide access through annular spacer 20 and conformal pad 12 to electronics 22.

Figure 9:
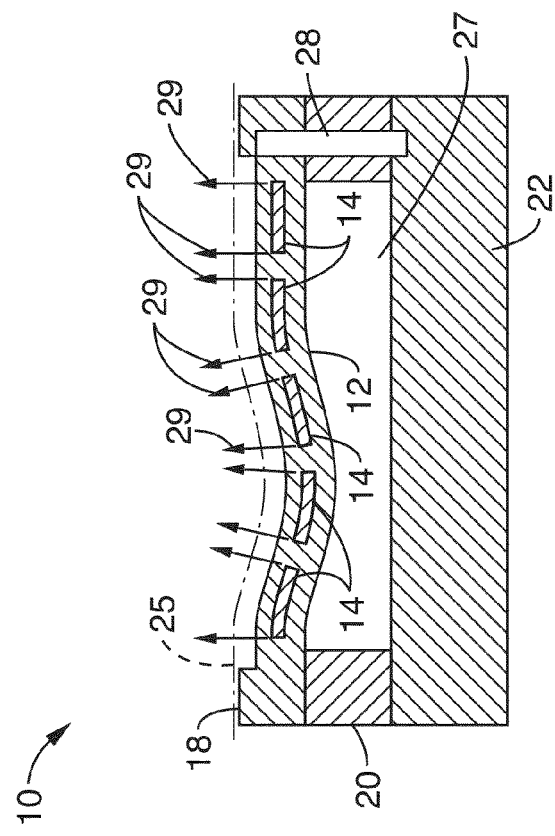
FIG. 9 illustrates a schematic side view of the SEM scanner of FIG. 8 in contact with subject skin.

FIG. 9 illustrates a schematic side view of the SEM scanner 10 in contact with the target subject 25. The annular silicone spacer 20 provides enough spacing for conforming silicone pad 12 to conform to the target surface 25. The conforming silicone pad 12 enables continuous contact between the substrate 16 and patient's skin 25, thus minimizing gaps between the substrate 16 and patient's skin 25 that could otherwise result in improper readings of the patient anatomy. Electrode array 14, which is embedded in substrate 16, is shown interrogating into the derma of tissue 25 by directing emission of an RF signal or energy into the skin and receiving the signal and correspondingly reading the reflected signal. The interrogator or electronics package 22 excites electrode coil 14 by providing the needed energy burst to support the scanning/reading of the tissue. Each embedded electrode 14 measures the equivalent sub-epidermal capacitance corresponding to the moisture content of the target skin 25.

While other energy modalities are contemplated (e.g. ultrasound, microwave, etc.), RF is generally preferred for its resolution in SEM scanning.

FIG. 10 illustrates a perspective view of an assembled SEM scanner 10 with an alternative substrate 16*b* having an array 14 of ten sensors dispersed within the substrate 16*b*. This larger array 14 provides for a larger scanning area of the subject anatomy, thus providing a complete picture of the target anatomy in one image without having to generate a scanning motion. It is appreciated that array 14 may comprise any number of individual sensors, in be disposed in a variety of patterns.

The SEM scanner 10 was evaluated using a number of different sized and types of sensors 26. Table 1 illustrates electrode geometries are used throughout the following measurements. As shown in FIG. 1 the outer ring electrode diameter $D_o$ varied from 5 mm for the XXS pad, to 55 mm for the large pad. The outer ring electrode inner diameter $D_I$ varied from 4 mm for the XXS pad, to 40 mm for the large pad. The inner electrode diameter $D_C$ varied from 2 mm for the XXS pad, to 7 mm for the large pad. It is appreciated that the actual dimensions of the electrodes may vary from ranges shown in these experiments. For example, the contact diameter may range from 5 mm to 30 mm, and preferably ranges from 10 mm to 20 mm.

To measure the properties of each sensor size listed in Table 1, the sensors were fabricated using both Kapton and rigid board. In testing with the rigid sensor pads, lotion was applied to the thumb continuously for 15 minutes.

Figure 11:
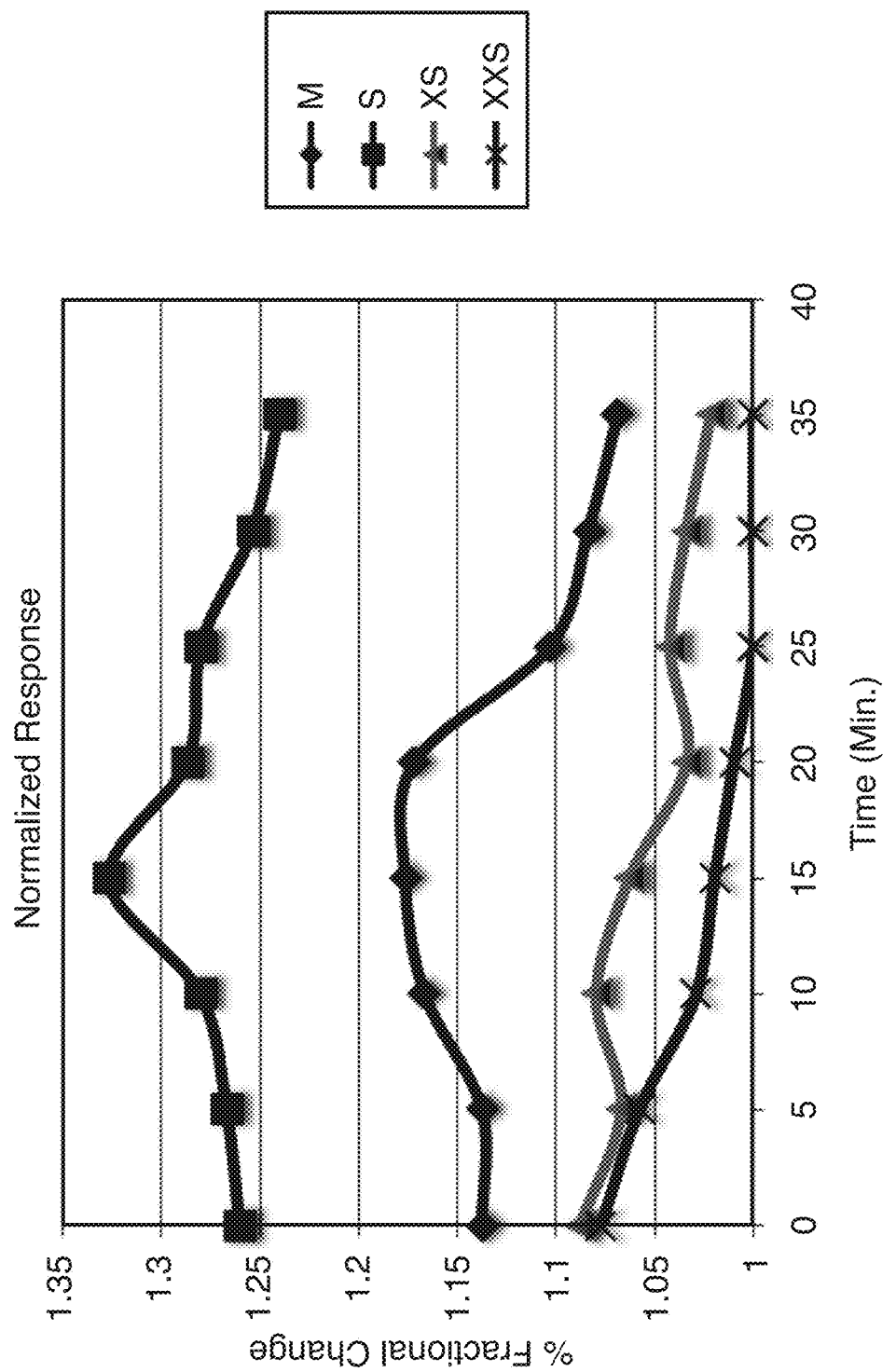
FIG. 11 is a plot of normalized responses of the tested electrodes of the present invention.

FIG. 11 is a plot of normalized responses of the tested electrodes of the present invention. The four sensors' (XXS, XS, S, M) normalized responses are compared in FIG. 11 and Table 2.

As can be seen in FIG. 11 and Table 2, the S electrode appears to be most responsive overall to the presence of moisture. Both the M and S electrodes seem to exhibit a peak. This suggests a depth dependency of the moisture being absorbed into the skin, as the roll-off from the M electrode occurs about 5 minutes after the peak for S electrode.

The SEM scanner 10 was also tested on the inner arm. A resistive pressure sensor (e.g. sensor 11 shown in FIG. 7) was also used to measure pressure applied on sensor to the arm. This way, constant pressure is applied across measurements. First, the dry inner arm was measured using the XS, S and M electrodes. Then, the same area was masked off with tape, and moisturizer lotion was applied for 30 minutes. Subsequent measurements were made on the same location after cleaning the surface.

Figure 12:
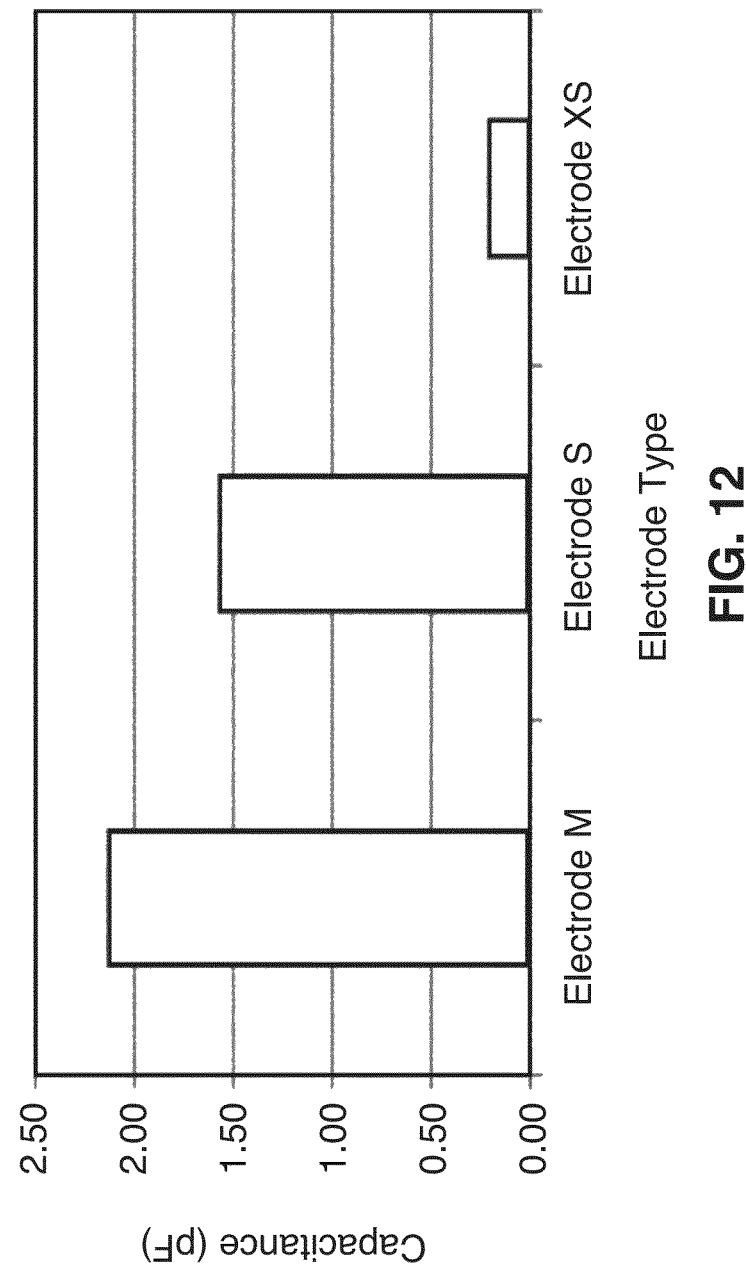
FIG. 12 is a graph of measured equivalent capacitance for dry volar arm for three different concentric sensor electrodes.

FIG. 12 is a graph of measured equivalent capacitance for dry Volar arm for three different sized (M, S, XS) concentric sensor electrodes before applying the commercial lotion moisturizer.

Figure 13:
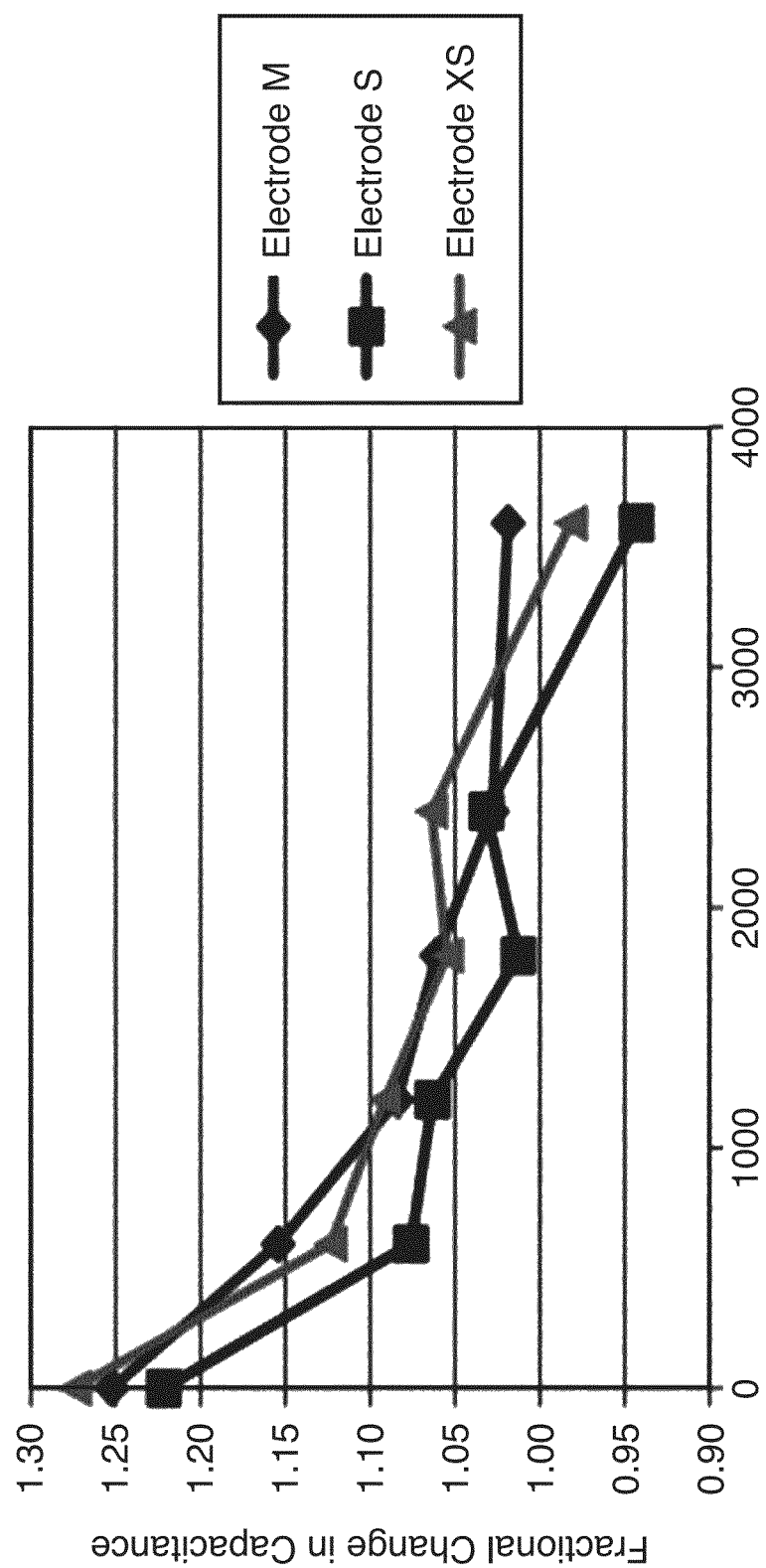
FIG. 13 is a plot of time dependent fractional change in capacitance relative to dry skin for three different concentric sensor electrodes (after 30 minutes of applying lotion).

FIG. 13 is a plot of time dependent fractional change in capacitance relative to dry skin for three different concentric sensor electrodes (after 30 minutes of applying lotion).

Figure 14:
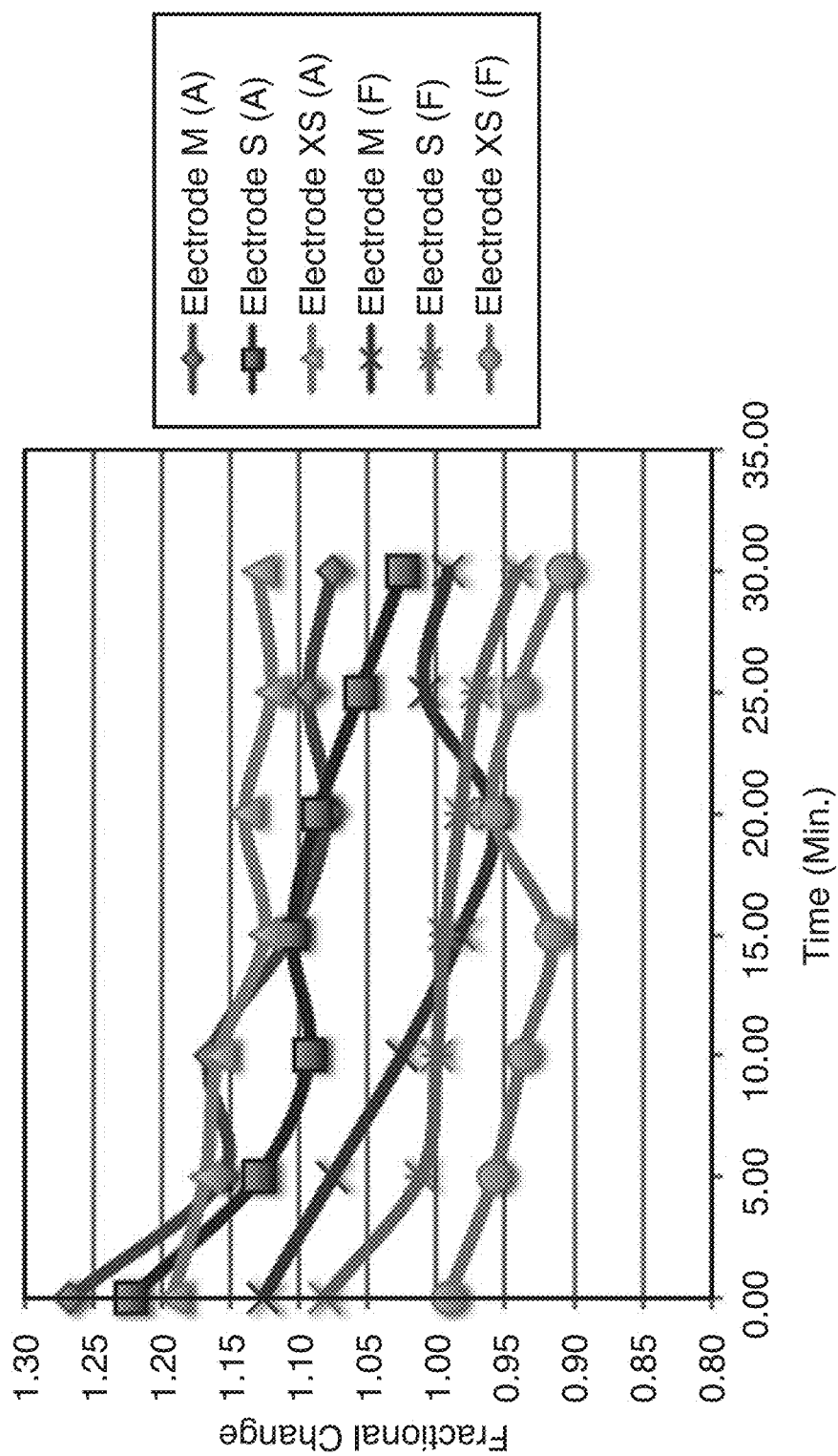
FIG. 14 is a plot of time dependent fractional change in capacitance relative to dry skin for three different concentric sensor electrodes (after 15 minutes of applying lotion).

FIG. 14 is a plot of time dependent fractional change in capacitance relative to dry skin for three different concentric sensor electrodes (after 15 minutes of applying lotion) on two subjects. This experiment was performed with faster sampling intervals and with lotion applied for 15 minutes only on forearms of two test subjects. Again, a resistive pressure sensor was used to measure pressure applied on sensor to the arm. This way, constant pressure is applied across measurements. First the dry inner arm was measured using the XS, S and M electrodes. Then the same area was masked off with tape, and lotion was applied for 15 minutes. Subsequent measurements were made on the same location every 5 minutes. Pressure was maintained at 50 k Ohms, and the forearm was tested again. We noticed an interesting observation for the case "F" in comparison to case "A" and also compared to previous measurements. Case "F" took a shower right before running the measurements and hence as a result his skin was relatively saturated with moisture. As a result, we observed less degree of sensitivity to the applied deep moisturizer for case "F".

The experiment was performed again for case "F", with a time resolution of 3 minutes, knowing that the subject did not shower in the morning before the test. The lotion was applied to the inner forearm for 15 minutes. Pressure was maintained at 50 k Ohms. The results confirm the sensitivity of the measurement to the residual skin moisture.

Figure 15:
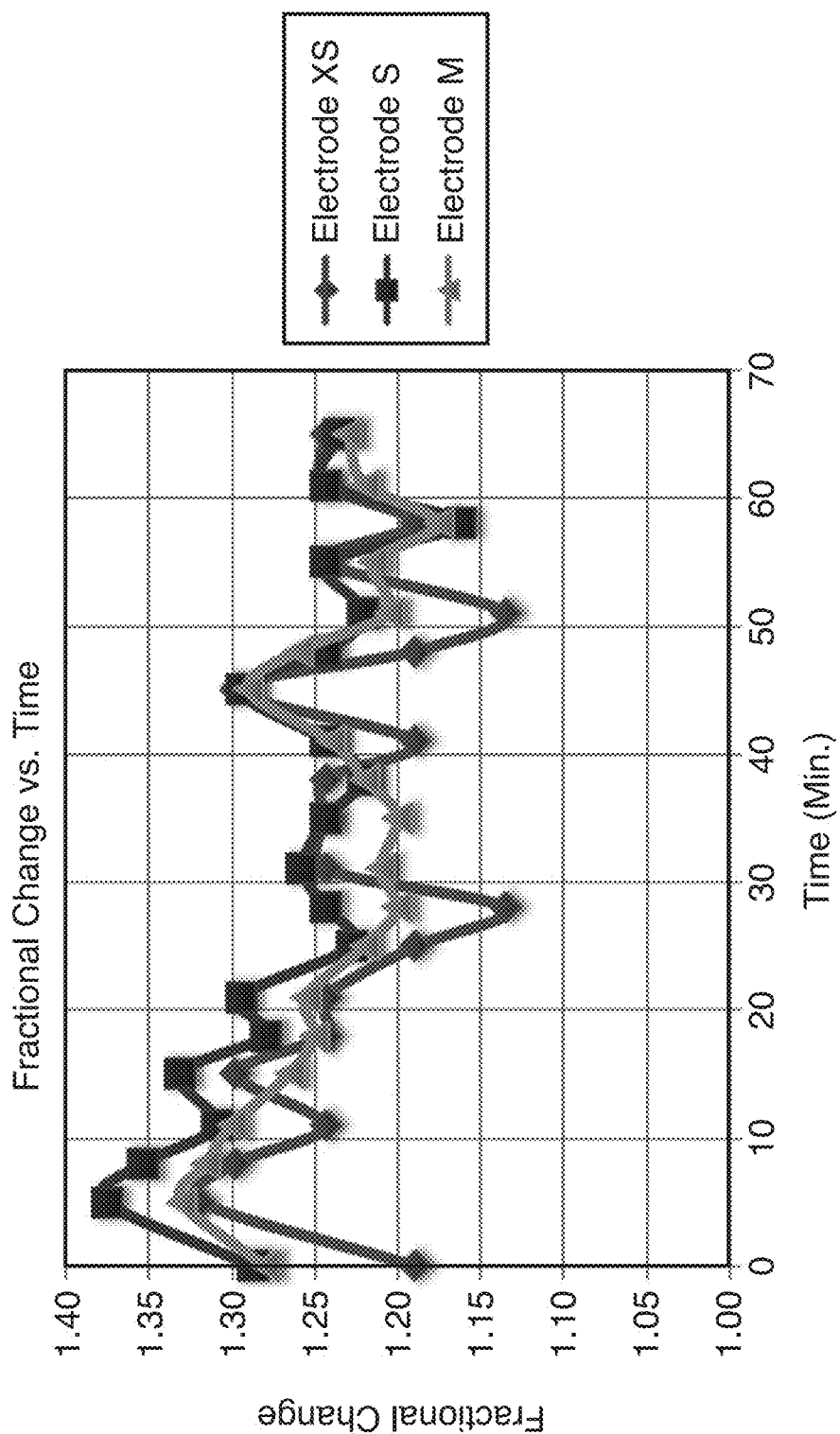
FIG. 15 is a plot of fractional change vs. time.

FIG. 15 is a plot of results for fractional change vs. time for M, S and XS electrodes.

Figure 16:
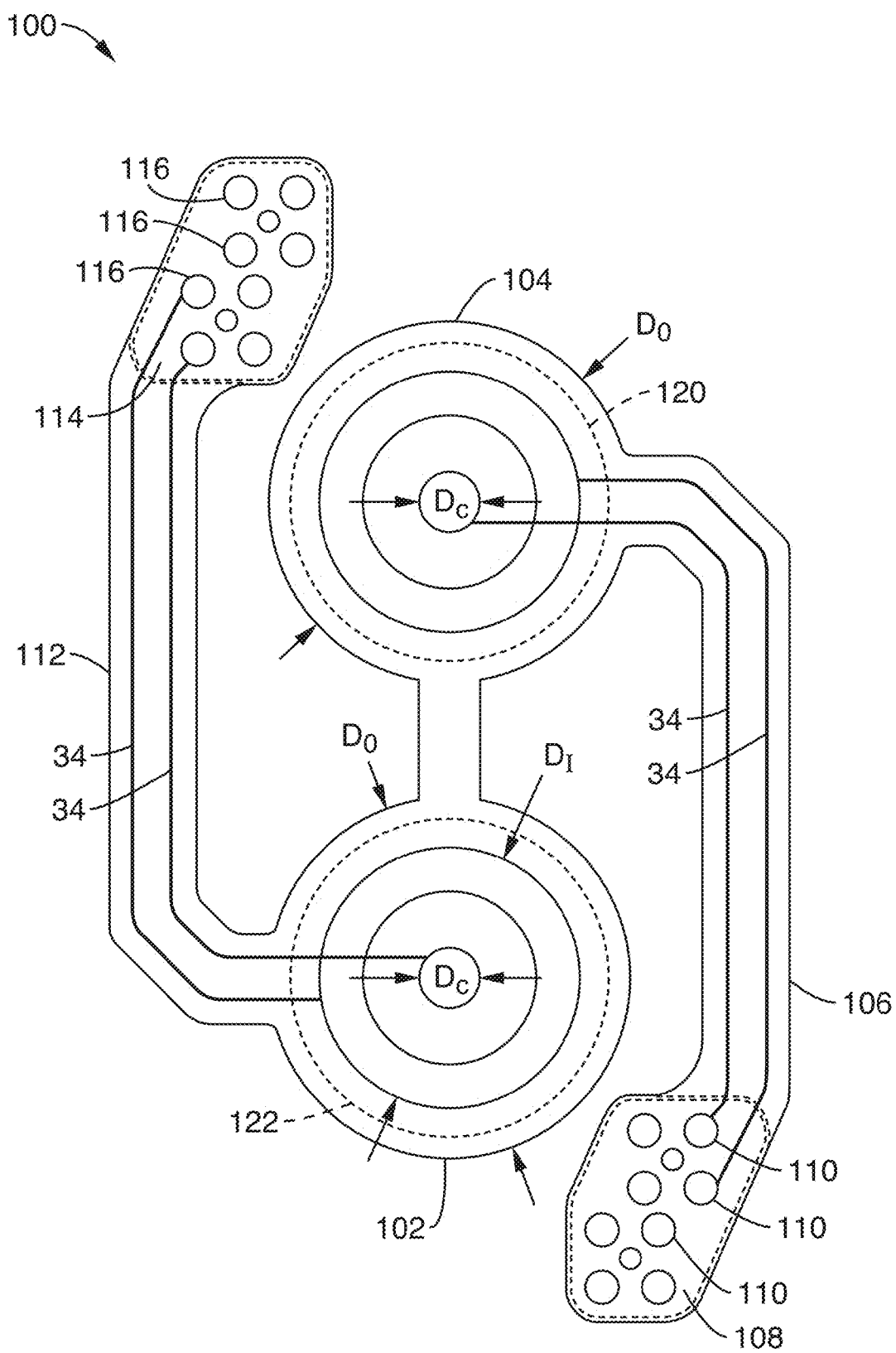
FIG. 16 shows a SEM scanner electrode system and electrode layering providing proper shielding from interference.

FIG. 16 shows a preferred embodiment of a layered SEM scanner electrode system 100 having a first electrode pad 102 and second electrode pad 104. Pad 104 is connected to lead line inputs 116 via wiring 34 along curved path 112. Pad 102 is connected to lead line inputs 110 via wiring 34 along curved path 106. A stiffener layer (e.g. layer 126 in FIG. 5) is provided directly under lead inputs 110 and 116 (see footprint 108 and 114 respectively) and under pads 102 and 104 (see footprint 122 and 120 respectively).

In this embodiment, the electrode size is approximately 2300 in width by 3910 mil in height.

Figure 17:
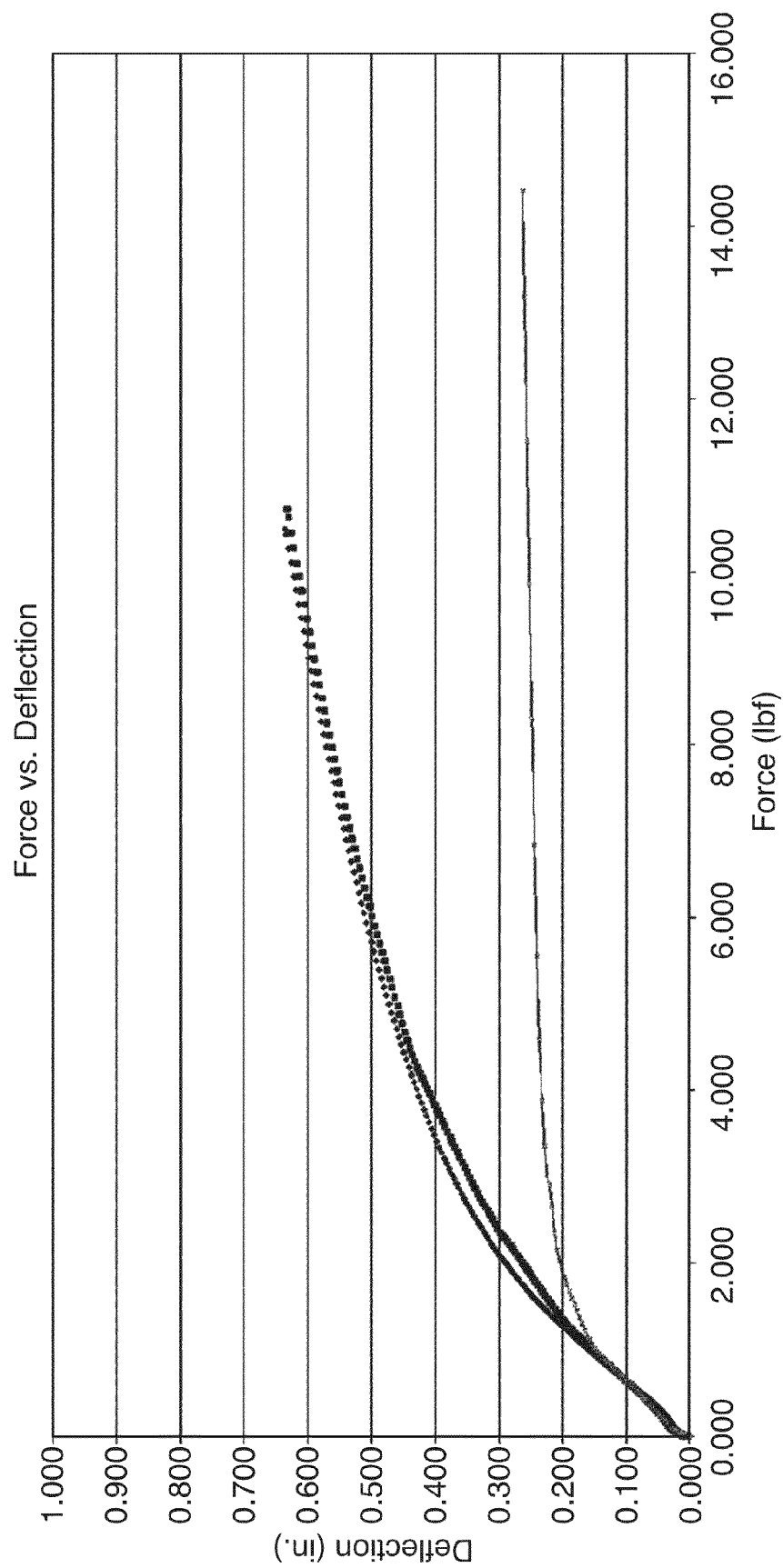
FIG. 17 shows an SEM scanner mechanical compliance for electrodes developed to enable probing of bony prominence.

FIG. 17 illustrates the SEM Scanner mechanical compliance (force-displacement relationship) for electrodes of system 100, developed to enable probing of bony prominence. The diamond symbols show the upper electrode 104 response, square symbols show the lower electrode 102 response.

The SEM scanner device 10 may also include other instruments, such as a camera (not shown), which can be used to take pictures of the wound, or develop a scanning system to scan barcodes as a login mechanism or an interrogator.

Patients using the SEM scanner device 10 may wear a bracelet (not shown) that contains data relating to their patient ID. This ID can be scanned by the camera embedded in the SEM scanner 10 to confirm correct patient ID correspondence. Alternatively, a separate RF scanner (not shown) may be used for interrogating the bracelet (in addition to the camera).

The SEM scanner device 10 is preferably ergonomically shaped to encourage correct placement of the device on desired body location.

The SEM Scanner device 10 of the present invention is capable of generating physical, absolute measurement values, and can produce measurements at multiple depths.

Figure 18:
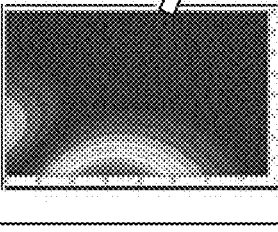
FIG. 18 is an overview of the wound registration method according to an embodiment of the description.

FIG. 18 shows the mapping function used to transform the target image.

In one embodiment of the description, wound images are obtained from a smart patch, which is able to retrieve multiple types of images from the same wound scan, including a moisture map and a pressure map of the bony prominence. This is summarized in FIG. 19.

Note the difference in our registration method from the previous work is that the two images can be significantly different from each other, due to the changes in wound healing. Additionally, we are aided from pressure readings obtained from the smart patch, which allow the improved registration of the more pertinent moisture maps. Bony prominence can be used in the feature detection phase.

Figure 19:
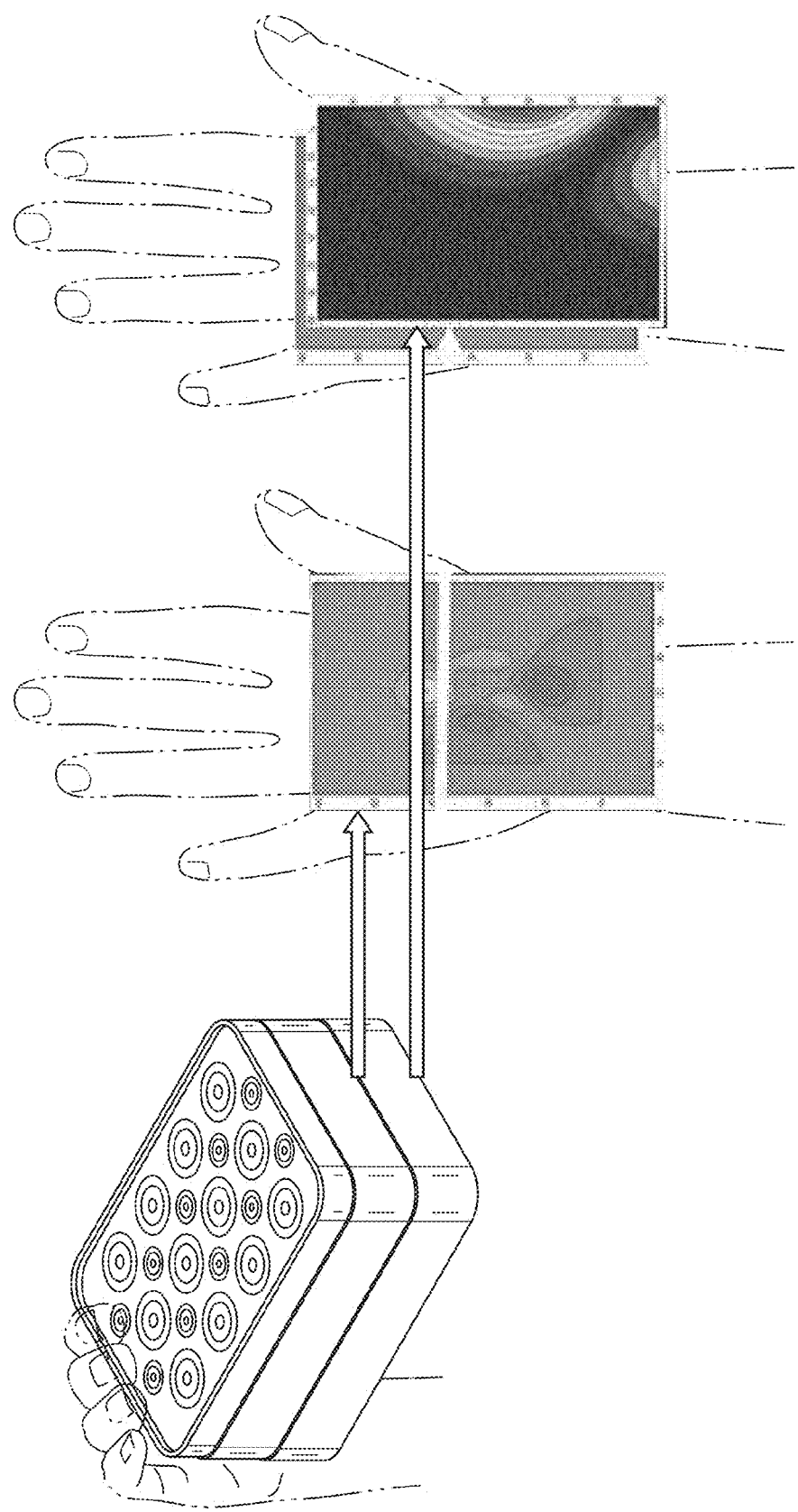
FIG. 19 illustrates pressure and moisture measurements obtained according to an embodiment of the description.
Figure 20:
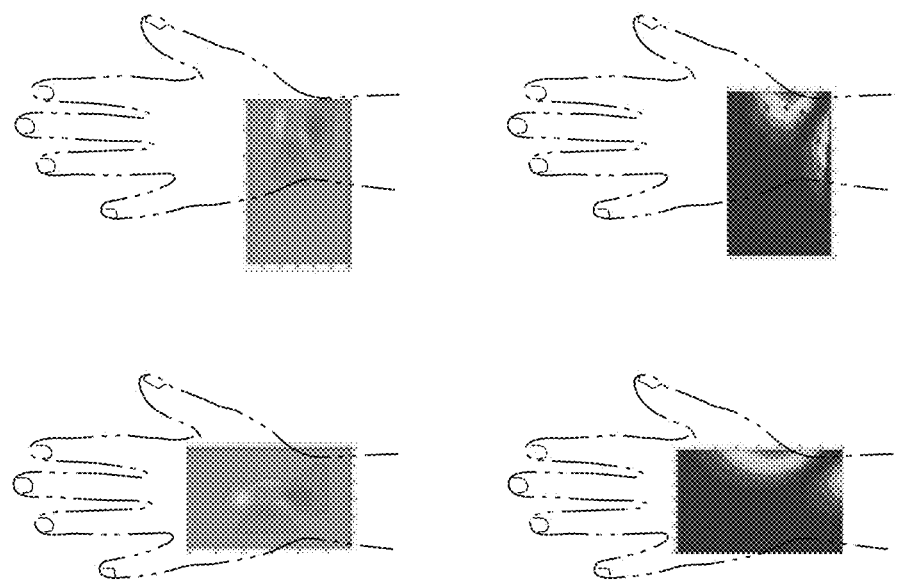
FIG. 20 illustrates sample measurements over two different days.

FIG. 19 demonstrates how both pressure and moisture measurements are obtained from the wound. This enables the registration of two different readings, obtained on two different days as shown in FIG. 20. The left column shows the reading, including pressure and moisture, from day 1 and the right column shows the reading from day 2. Note the images obtained are severely misaligned.

From the foregoing it will be appreciated that the present invention can be embodied in various ways, which include but are not limited to the following:

1. An apparatus for sensing sub-epidermal moisture from a location external to a patient's skin, comprising: a bipolar RF sensor embedded on a flexible substrate; a conformal pressure pad disposed adjacent and underneath the substrate; wherein the conformal pressure pad is configured to support the flexible substrate while allowing the flexible substrate to conform to a non-planar sensing surface of the patient's skin; and interface electronics coupled to the sensor; wherein said interface electronics is configured to control emission and reception of RF energy to interrogate the patient's skin.

2. The apparatus of embodiment 1, further comprising: an annular spacer adjacent and underneath the conformal pressure pad; wherein the annular spacer comprises a central opening configured to allow the conformal pressure pad to deflect freely into the central opening.

3. The apparatus of embodiment 1, further comprising: an array of bipolar RF sensors spaced across the flexible substrate; wherein each of the sensors is independently coupled to the interface electronics to independently interrogate the patient's skin.

4. The apparatus of embodiment 3: wherein each of the sensors is configured to measure an equivalent sub-epidermal capacitance of a target region of skin; said sub-epidermal capacitance corresponding to the moisture content of the target region of skin.

5. The apparatus of embodiment 4: wherein the array of sensors comprises a first sensor having a first contact area and a second sensor having a second contact area larger than the first sensor; wherein the first and second sensors interrogate the skin at different depths.

6. The apparatus of embodiment 4: wherein the substrate comprises a substrate assembly comprising a substrate layer; and wherein the sensor comprises a sensing pad having a first electrode embedded on a first side of the substrate and a second electrode embedded on a second side of the substrate.

7. The apparatus of embodiment 6, further comprising a biocompatible cover layer disposed over said first side of said substrate layer.

8. The apparatus of embodiment 6, further comprising a cover layer disposed under said second side of said substrate layer.

9. The apparatus of embodiment 6, further comprising a stiffener layer disposed under said second side of said substrate layer; wherein the stiffener layer comprises a footprint substantially similar to that of the sensor array.

10. The apparatus of embodiment 6: wherein said first electrode comprises an annular ring having an inner radius and an outer radius; wherein said second electrode comprises an outer radius having a smaller diameter than the inner radius of the first electrode; and wherein said second electrode is concentric with said first radius.

11. The apparatus of embodiment 1, wherein the interface electronics are configured to transmit data retrieved from said sensors.

12. The apparatus of embodiment 4, further comprising: a pressure sensor positioned in line with said RF sensor; said pressure sensor configured to measure an applied pressure of the substrate at a location on the patient's skin.

13. The apparatus of embodiment 1, wherein the flexible substrate comprises Kapton or Polyimide.

14. A scanner for sensing sub-epidermal moisture from a location external to a patient's skin, comprising: an array of bipolar RF sensors embedded on a flexible substrate; and a conformal pressure pad disposed adjacent and underneath the substrate; wherein the conformal pressure pad is configured to support the flexible substrate while allowing the flexible substrate to conform to a non-planar sensing surface of the patient's skin; wherein said sensor array is configured to emit and receive RF energy to interrogate the patient's skin; and wherein each of the sensors are independently are individually wired to independently interrogate the patient's skin.

15. The scanner of embodiment 14, further comprising: interface electronics coupled to the sensor; wherein said interface electronics is configured to control the emission and reception of RF energy.

16. The scanner of embodiment 14, further comprising: an annular spacer adjacent and underneath the conformal pressure pad; wherein the annular spacer comprises a central opening configured to allow the conformal pressure pad to deflect freely into the central opening.

17. The scanner of embodiment 14: wherein each of the sensors is configured to measure an equivalent sub-epidermal capacitance of a target region of skin; said sub-epidermal capacitance corresponding to the moisture content of the target region of skin.

18. The scanner of embodiment 14: wherein the array of sensors comprises a first sensor having a first contact area and a second sensor having a second contact area larger than the first sensor; and wherein the first and second sensors interrogate the skin at different depths.

19. The scanner of embodiment 14: wherein each sensor comprises a first electrode in the form of an annular ring having an inner radius and an outer radius and a second electrode comprising an outer radius having a smaller diameter than the first electrode; and wherein said second electrode is concentric with said first radius.

20. The scanner of embodiment 19: wherein the substrate comprises a substrate assembly comprising a substrate layer; and wherein the first electrode is embedded on a first side of the substrate and the second electrode embedded on a second side of the substrate.

21. The scanner of embodiment 20, further comprising: an upper biocompatible cover layer disposed over said first side of said substrate layer and a lower cover layer disposed under said second side of said substrate layer.

22. The scanner of embodiment 20, further comprising: a stiffener layer disposed under said second side of said substrate layer; wherein the stiffener layer comprises a footprint substantially similar to that of the sensor array.

23. The scanner of embodiment 14, further comprising: an array of pressure sensors positioned in line with said RF sensor; said pressure sensors are configured to measure an applied pressure of the substrate at corresponding locations on the patient's skin.

24. A method for monitoring the formation of pressure ulcers at a target location of a patient's skin, comprising: positioning a flexible substrate adjacent the target location of the patient's skin; the flexible substrate comprising one or more bipolar RF sensors; conforming the flexible substrate to the patient's skin at the target location; exciting the one or more bipolar RF sensor to emit RF energy into the patient's skin; and measuring the capacitance of the skin at the target location as an indicator of the Sub-Epidermal Moisture (SEM) at the target location.

25. The method of embodiment 24: wherein the one or more sensors comprise an array of sensors disposed across said substrate; and wherein the one or more sensors are individually controlled to independently excite the one or more sensors.

26. The method of embodiment 24, further comprising: measuring an applied pressure of the substrate at the target location on the patient's skin.

27. The method of embodiment 25, further comprising: measuring an applied pressure of the substrate on the patient's skin at each of the sensors in the array.

Although the description above contains many details, these should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

TABLE 1

| Symbol | XXS | XS | S | M | L |
| --- | --- | --- | --- | --- | --- |
| Contact Diameter (mm) | 5 | 10 | 20 | 23 | 55 |
| Approx Outer $D_o$ (mm) | 5 | 10 | 20 | 23 | 55 |
| Approx Middle $D_i$ (mm) | 4 | 6 | 10 | 15 | 40 |
| Approx Inner $D_c$ (mm) | 2 | 2 | 4 | 5 | 7 |

TABLE 2

| Tabulated Normalized Responses of M, S, XS and XXS Electrodes | | | | | | | | |
| --- | --- | --- | --- | --- | --- | --- | --- | --- |
| Time | M | M Baseline | S | S Baseline | XS | XS Baseline | XXS | XXS Baseline |
| 0 | 2.32 | 2.04 | 1.89 | 1.5 | 0.261 | 0.24 | 1.12 | 1.04 |
| 5 | 2.32 | 2.04 | 1.9 | 1.5 | 0.256 | 0.24 | 1.1 | 1.04 |
| 10 | 2.38 | 2.04 | 1.92 | 1.5 | 0.259 | 0.24 | 1.07 | 1.04 |
| 15 | 2.4 | 2.04 | 1.99 | 1.5 | 0.255 | 0.24 | 1.06 | 1.04 |
| 20 | 2.39 | 2.04 | 1.93 | 1.5 | 0.248 | 0.24 | 1.05 | 1.04 |
| 25 | 2.25 | 2.04 | 1.92 | 1.5 | 0.25 | 0.24 | 1.04 | 1.04 |
| 30 | 2.21 | 2.04 | 1.88 | 1.5 | 0.248 | 0.24 | 1.04 | 1.04 |
| 35 | 2.18 | 2.04 | 1.86 | 1.5 | 0.245 | 0.24 | 1.04 | 1.04 |

What is claimed is:

1. A scanner for sensing sub-epidermal moisture from a location external to a patient's skin, said scanner comprising:

an array of bipolar radiofrequency (RF) sensors embedded on a flexible substrate comprising a substrate layer;

wherein each bipolar RF sensor in said array comprises a first electrode in the form of an annular ring having an inner diameter and an outer diameter and a second electrode comprising an outer radius having a diameter smaller than the inner diameter of the first electrode;

wherein said second electrode is concentric with said first electrode;

wherein said first electrode is embedded on a first side of said substrate layer and wherein said second electrode is embedded on a second side of said substrate layer;

wherein said array of bipolar RF sensors is configured to emit and receive RF energy to interrogate into the derma of the patient's skin to sense sub-epidermal moisture; and wherein each of the bipolar RF sensors are individually wired to independently interrogate into the derma of the patient's skin; and wherein each of the bipolar RF sensors in said array is configured to measure an equivalent sub-epidermal capacitance of a target region of skin; and wherein said sub-epidermal capacitance corresponds to the moisture content of the target region of skin.

2. The scanner as recited in claim 1, further comprising interface electronics coupled to the array of sensors, wherein said interface electronics is configured to control the emission and reception of RF energy by the bipolar RF sensor.

3. The scanner as recited in claim 1, wherein said array of bipolar RF sensors comprises a first sensor having a first contact area and a second sensor having a second contact area larger than the first sensor; and wherein said first and second sensors interrogate the skin at different depths.

4. The scanner as recited in claim 1, further comprising an upper biocompatible cover layer disposed over said first side of said substrate layer and a lower cover layer disposed under said second side of said substrate layer.

5. The scanner as recited in claim 1, further comprising:

a stiffener layer disposed under said second side of said substrate layer;

wherein the stiffener layer comprises a footprint substantially similar to that of the sensor array.

6. The scanner as recited in claim 1, further comprising:

an array of pressure sensors positioned in line with said array of bipolar RF sensors;

wherein said pressure sensor is configured to measure an applied pressure of the flexible substrate at corresponding locations on the patient's skin.

7. The scanner as recited in claim 1, wherein said array of bipolar RF sensors is configured to measure sub-epidermal moisture for generating a sub-epidermal moisture image of the surface of the patient's skin without using a scanning motion.

8. The scanner as recited in claim 1, wherein the flexible substrate comprises Kapton® or Polyimide.

9. An apparatus for sensing sub-epidermal moisture from a location external to a patient's skin, said apparatus comprising:

a bipolar radiofrequency (RF) sensor embedded on a flexible substrate comprising a substrate layer;

wherein said bipolar RF sensor comprises a sensing pad having a first electrode embedded on a first side of said substrate layer and a second electrode embedded on a second side of said substrate layer;

a conformal pressure pad disposed adjacent and beneath said flexible substrate, wherein said conformal pressure pad is configured to support said flexible substrate while allowing said flexible substrate to conform to a non-planar sensing surface of the patient's skin; and interface electronics coupled to the bipolar RF sensor, wherein said interface electronics are configured to control emission and reception of RF energy by the bipolar RF sensor to interrogate into the derma of the patient's skin to sense sub-epidermal moisture; and wherein said bipolar RF sensor is configured to measure an equivalent sub-epidermal capacitance of a target region of skin; and wherein said sub-epidermal capacitance corresponds to the moisture content of the target region of skin.

10. The apparatus as recited in claim 9, further comprising:
an annular spacer adjacent and underneath said conformal pressure pad;
wherein said annular spacer comprises a central opening configured to allow said conformal pressure pad to deflect freely into said central opening.

11. The apparatus as recited in claim 9, further comprising a biocompatible cover layer disposed over said first side of said substrate layer.

12. The apparatus as recited in claim 9, further comprising a cover layer disposed under said second side of said substrate layer.

13. The apparatus as recited in claim 9, further comprising:
a stiffener layer disposed under said second side of said substrate layer;
wherein the stiffener layer comprises a footprint substantially similar to that of the bipolar RF sensor.

14. The apparatus as recited in claim 9:
wherein said first electrode comprises an annular ring having an inner diameter and an outer diameter, wherein said second electrode comprises a diameter smaller than the inner diameter of the first electrode; and
wherein said second electrode is concentric with said first radius.

15. The apparatus as recited in claim 9, wherein the interface electronics are configured to transmit data retrieved from said bipolar RF sensor.

16. The apparatus as recited in claim 9, further comprising:
a pressure sensor positioned in line with said bipolar RF sensor;
said pressure sensor configured to measure an applied pressure of the flexible substrate at a location on the patient's skin.

17. The apparatus as recited in claim 9, wherein the flexible substrate comprises Kapton® or Polyimide.

* * * * *